United States Patent
Naaman et al.

(10) Patent No.: US 8,957,460 B2
(45) Date of Patent: Feb. 17, 2015

(54) PROTEIN DETECTOR BASED ON MOLECULAR CONTROLLED SEMICONDUCTOR RESISTOR

(75) Inventors: Ron Naaman, Yarkona (IL); Eyal Capua, Rehovot (IL); Danny Bavli, Rehovot (IL); Maria Tkachev, Rehovot (IL)

(73) Assignee: Yeda Research and Development Co. Ltd. (IL)

( * ) Notice: Subject to any disclaimer, the term of this patent is extended or adjusted under 35 U.S.C. 154(b) by 0 days.

(21) Appl. No.: 14/124,313

(22) PCT Filed: May 31, 2012

(86) PCT No.: PCT/IL2012/000215
§ 371 (c)(1),
(2), (4) Date: Feb. 19, 2014

(87) PCT Pub. No.: WO2012/168932
PCT Pub. Date: Dec. 13, 2012

(65) Prior Publication Data
US 2014/0170675 A1    Jun. 19, 2014

Related U.S. Application Data

(60) Provisional application No. 61/493,637, filed on Jun. 6, 2011.

(51) Int. Cl.
*H01L 21/00*       (2006.01)
*G01N 27/49*       (2006.01)
(Continued)

(52) U.S. Cl.
CPC .................................. *G01N 27/4145* (2013.01)
USPC .............................. 257/253; 257/414; 438/49

(58) Field of Classification Search
USPC ..................................... 257/253, 414; 438/49
See application file for complete search history.

(56) References Cited

U.S. PATENT DOCUMENTS

4,437,969 A  *  3/1984  Covington et al. ............ 257/253
4,716,448 A  *  12/1987  Kelly ............................. 257/253
(Continued)

FOREIGN PATENT DOCUMENTS

WO           9819151          5/1998

OTHER PUBLICATIONS

International Search Report for corresponding application PCT/IL2012/000215 filed May 31, 2012; Mail date Sep. 6, 2012.
(Continued)

*Primary Examiner* — Evan Pert
(74) *Attorney, Agent, or Firm* — Cantor Colburn LLP

(57) ABSTRACT

The invention provides a semiconductor device for the detection of an active site-containing protein or a ligand thereof in a solution, said device comprising at least one insulating or semi-insulating layer; at least one conducting semiconductor layer; two conducting pads on top of the upper layer making electrical contact with said at least one conducting semiconductor layer, such that electrical current can flow between them at a finite distance from the surface of the device; a protective molecular layer fabricated on top of said upper layer and protecting said layer from corrosion; and said ligand or active site-containing protein linked to said protective molecular layer. Exposure of said ligand or active site-containing protein to a solution containing said active site-containing protein or ligand, respectively, causes a current change through the device when a constant electric potential is applied between the two conducting pads. The semiconductor device can be seen as a molecularly controlled semiconductor resistor (MOCSER) protein sensor based on doped and undoped GaAs stack structure. The GaAs is protected against etching in aqueous environments by the protective molecular layer.

20 Claims, 20 Drawing Sheets

(51) Int. Cl.
H01L 27/28 (2006.01)
G01N 27/414 (2006.01)

(56) References Cited

U.S. PATENT DOCUMENTS

| | | | |
|---|---|---|---|
| 5,077,229 A * | 12/1991 | Forlani | 438/49 |
| 7,118,861 B1 | 10/2006 | Naaman et al. | |
| 7,948,015 B2 * | 5/2011 | Rothberg et al. | 257/253 |
| 8,262,900 B2 * | 9/2012 | Rothberg et al. | 205/793.5 |
| 2009/0026082 A1 * | 1/2009 | Rothberg et al. | 204/556 |
| 2013/0292743 A1 * | 11/2013 | Rothberg et al. | 257/253 |

OTHER PUBLICATIONS

Capua et al; "The molecularly controlled semiconductor resistir: How does it work?", ACS Applied Materials & Interfaces, 1(11), pp. 2679-2683. (2009).

Kirchner et al; "Corrosion protection and long-term chemical functionalization of gallium arsenide in an aqueous environment" Advanced Functional Materials, 12(4), pp. 266-276. (2004).

Written Opinion for corresponding application PCT/IL2012/000215 filed May 31, 2012; Mail date Sep. 6, 2012.

International Preliminary Report on Patentability for corresponding application PCT/IL2012/000215 filed May 31, 2012; Mail date Dec. 27, 2013.

* cited by examiner

PROTEIN DETECTOR BASED ON MOLECULAR CONTROLLED SEMICONDUCTOR RESISTOR

TECHNICAL FIELD

The present invention relates to semiconductor devices for detection and/or quantification of proteins, more particularly active site-containing proteins, or ligands thereof, more specifically to such devices based on molecular controlled semiconductor resistors.

BACKGROUND ART

The detection of covalent and noncovalent binding events between molecules and biomembranes is a fundamental goal of contemporary biochemistry and analytical chemistry. This detection serves for the basic study of central biological processes like signaling, and for the development of high throughput screening of drug candidates from large libraries of molecules that potentially recognize a specific membrane receptor. Currently, such studies are performed routinely using fluorescence methods (Chattopadhyay and Raghuraman, 2004), surface-plasmon resonance (SPR) spectroscopy (Baciu et al., 2008), and electrochemical methods (Thompson and Krull, 1982; Thompson et al., 1983; Umezawa et al., 1988; Woodhouse et al., 1999; Xu and Bakker, 2009; Dumas et al., 2011; Coldrick et al., 2011). However, there is still need for novel sensitive miniaturizable detection methods, e.g., for point-of-care testing (POCT).

The preparation and characterization of model membranes on solid supports, e.g., semiconductors, is a practical and scientifically important research area (Tanaka and Sackmann, 2005). Practical applications include smart biosensor devices for studying basic membrane processes and membrane-analyte interactions, as well as for other biotechnological applications (Bieri et al., 1999; Sackmann and Tanaka, 2000; Sapuri et al., 2002; Yip et al., 2002).

Recent advances in microelectronics and nanotechnology, improvement in sensor function, and emergence of new types of biosensors have increased the interest in development of lipid membrane-based systems. Electrochemical methods were applied since they allow direct conversion of biological information to electronic signal. They are well suited for investigation of biomembrane functions due to their operation simplicity, low cost, and capability of real-time measurements. Typically, electrochemical biosensors employ amperometric, potentiometric, or impedimetric transducers (Thompson and Krull, 1982; Thompson et al., 1983; Umezawa et al., 1988; Woodhouse et al., 1999; Xu and Bakker, 2009; Dumas et al., 2011; Coldrick et al., 2011).

Sensors based on field-effect transistor (FET) configuration have been utilized since the early 1970s (Bergveld, 1972; Bergveld et al., 1978). This special class of sensors makes use of the potentiometric effect at a gate electrode (Thevenot et al., 2001). Currently, biosensing applications focus on ion-selective FET (ISFET or CHEMFET) devices. In ISFET, the regular gate is placed in a liquid electrolyte, and the diffusion of specific analytes toward the electrode can be controlled by insertion of a selective membrane positioned on the gate. ISFET approach was utilized, e.g., for studying enzyme-substrate recognition and for detecting neurons or living cell activity (Baumann et al., 1999; Kharitonov et al., 2000; Schoning and Poghossian, 2002; Bergveld, 2003; Janata, 2004). A theoretical model for biorecognition of acetylcholine applying enzyme-modified ISFET was provided recently (Goykhman et al., 2009). According to this model, the electrical response of the device, during enzyme-substrate recognition events, depends on cooperative effects of local pH changes and molecular dipole variations.

International Patent Publication No. WO 98/19151 (corresponding to U.S. Pat. No. 6,433,356) of the same applicant of the present invention, herewith incorporated by reference in its entirety as if fully disclosed herein, describes a hybrid organic-inorganic semiconductor device and sensors based thereon, said device characterized by being composed of: (i) at least one layer of a conducting semiconductor; (ii) at least one insulating layer, (iii) a multifunctional organic sensing molecule directly chemisorbed on one of its surfaces, said multifunctional organic sensing molecule having at least one functional group that binds to the said surface of the electronic device, and at least one other functional group that serves as a sensor, and (iv) two conducting pads on the top layer making electrical contact with the electrically conducting layer, such that electrical current can flow between them at a finite distance from the surface of the device. The semiconductor devices disclosed in WO 98/19151 are referred to as molecular controlled semiconductor resistors (MOCSERs) and described as light or chemical sensors.

SUMMARY OF INVENTION

It has been found, in accordance with the present invention, that a device based on the molecular controlled semiconductor resistor (MOCSER) previously described (Gartsman et al., 1998; Vilan et al., 1998; Wu et al., 2000; Rei Vilar et al., 2006) and disclosed in the aforesaid WO 98/19151, when covered with a protective molecular layer fabricated on top of its upper layer that is either a conducting semiconductor layer or an insulating or semi-insulating layer, protecting said upper layer from corrosion, in particular, a protective molecular layer comprising an alkoxysilane-based polymer, can be used for detection of active site-containing proteins or ligands thereof in a solution, and can thus be utilized for monitoring processes occurring on a membrane and the interaction of an active site-containing protein in solution with a ligand thereof linked to said protective molecular layer, or vice versa.

In one aspect, the present invention thus relates to a semiconductor device for the detection of an active site-containing protein or a ligand thereof in a solution, said device being composed of at least one insulating or semi-insulating layer, at least one conducting semiconductor layer, two conducting pads, a protective molecular layer, and said ligand or active site-containing protein, wherein said at least one conducting semiconductor layer is on top of one of said insulating or semi-insulating layers, said two conducting pads are on both sides on top of an upper layer which is either one of said conducting semiconductor layers or another of said insulating or semi-insulating layers, making electrical contact with said at least one conducting semiconductor layer, said protective molecular layer is fabricated on top of said upper layer protecting said upper layer from corrosion, and said ligand or active site-containing protein is linked either directly or indirectly to said protective molecular layer, wherein exposure of said ligand or active site-containing protein, to a solution containing said active site-containing protein or ligand, respectively, causes a current change through the semiconductor device when a constant electric potential is applied between the two conducting pads.

In certain embodiments, the ligand or active site-containing protein is directly linked to the protective molecular layer of the semiconductor device of the present invention. In other embodiments, the ligand or active site-containing protein is indirectly linked to said protective molecular layer via a mono- or bi-layer membrane comprising an amphiphilic compound or a mixture thereof, wherein said mono- or bi-layer membrane is adhered to said protective molecular layer. In further embodiments, the ligand or active site-containing protein is indirectly linked to said protective molecular layer via a linker such as a ligand-binding protein, biotin, or a biotin-like molecule.

The semiconductor device of the present invention may further be used for quantification of said active site-containing protein or ligand thereof in the solution, wherein the current change through the semiconductor device when a constant electric potential is applied between the two conducting pads is proportional to the concentration of said active site-containing protein or ligand thereof in the solution.

In another aspect, the present invention provides a method for detection of an active site-containing protein or a ligand thereof in a solution, said method comprising:

(i) exposing a semiconductor device as defined above to said solution; and
(ii) monitoring the presence of said active site-containing protein or ligand in said solution according to the changes in the current measured in said semiconductor device when a constant electric potential is applied between the two conducting pads.

DETAILED DESCRIPTION OF THE INVENTION

Figure 1:
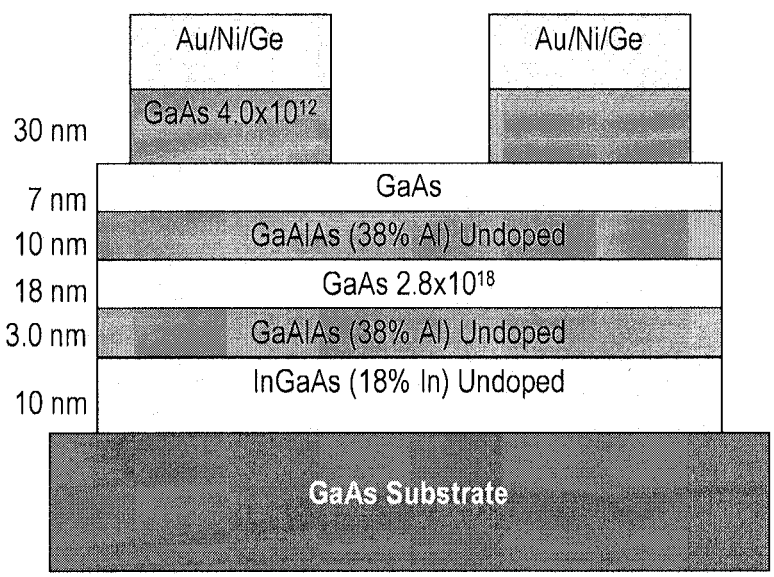
FIG. 1 shows a schematic representation of the GaAs pseudomorphic High Electron Mobility Transistor (pHEMT) structure used for the MOCSER fabrication.

In one aspect, the present invention provides a semiconductor device based on a molecular controlled semiconductor resistor (MOCSER) for the detection of an active site-containing protein or a ligand thereof in a solution, as defined above.

In one particular such aspect, the present invention provides a semiconductor device for the detection of said active site-containing protein in said solution, wherein said semiconductor device comprises said ligand linked either directly or indirectly to said protective molecular layer, and exposure of said ligand to a solution containing said active site-containing protein causes a current change through the semiconductor device when a constant electric potential is applied between the two conducting pads.

In another particular such aspect, the present invention provides a semiconductor device for the detection of said ligand in said solution, wherein said semiconductor device comprises said active site-containing protein linked either directly or indirectly to said protective molecular layer, and exposure of said active site-containing protein to a solution containing said ligand causes a current change through the semiconductor device when a constant electric potential is applied between the two conducting pads.

The term "active site-containing protein", as used herein, refers to a non-structural protein including, e.g., an antibody, protein antigen, enzyme, protein substrate or inhibitor, receptor, and lectin. The term "ligand", as used herein with respect to said active site-containing protein, refers to an ion, molecule, or molecular group that binds to said active site-containing protein as defined above to form a larger complex. Non-limiting examples of active site-containing protein-ligand pairs include an antibody and its antigen, respectively, or vice versa; an enzyme and either a substrate or inhibitor thereof, respectively, of vice versa; a receptor and either a protein or organic molecule, respectively, or vice versa; and a lectin and a sugar.

In one embodiment, the semiconductor device of the present invention is composed of at least one insulating or semi-insulating layer, one conducting semiconductor layer, two conducting pads, a protective molecular layer, and said ligand or active site-containing protein, wherein said conducting semiconductor layer is on top of one of said insulating or semi-insulating layers, said two conducting pads are on both sides on top of an upper layer which is either said conducting semiconductor layer or another of said insulating or semi-insulating layers, making electrical contact with said conducting semiconductor layer, said protective molecular layer is fabricated on top of said upper layer, and said ligand or active site-containing protein is linked either directly or indirectly to said protective molecular layer.

The various conducting semiconductor and insulating or semi-insulating layers of the semiconductor device of the present invention are defined as in the basic MOCSER disclosed in the aforesaid WO 98/19151.

In certain embodiments, each one of the conducting semiconductor layers in the semiconductor device of the present invention independently is a semiconductor selected from a III-V and a II-VI material, or mixtures thereof, wherein III, V, II and VI denote the Periodic Table elements III=Ga, In;

V=As, P; II=Cd, Zn; VI=S, Se, Te. In preferred embodiments, each one of the conducting semiconductor layers is doped GaAs or doped (Al,Ga)As.

In certain embodiments, each one of the insulating or semi-insulating layers in the semiconductor device of the present invention independently is a dielectric material selected from silicon oxide, silicon nitride or an undoped semiconductor selected from a III-V and a II-VI material, or mixtures thereof, wherein III, V, II and VI denote the Periodic Table elements III=Ga, In; V=As, P; II=Cd, Zn; VI=S, Se, Te. In preferred embodiments, the undoped semiconductor is undoped GaAs or undoped (Al,Ga)As.

The protective molecular layer of the semiconductor device of the present invention is aimed at protecting the device from etching, i.e., corrosion, in aqueous solutions.

In certain embodiments, the protective molecular layer comprises an alkoxysilane-based polymer, i.e., a polymer formed by polymerization of dialkoxysilanes, trialkoxysilanes or tetraalkoxysilanes, preferably trialkoxysilanes, each one of said alkoxysilanes having a functional group, a biotinylated form thereof, or a mixture of the aforesaid. In particular embodiments, the alkoxysilane-based polymer is formed by polymerization of dialkoxysilanes or trialkoxysilanes of the general formula $(C_1-C_7$ alkyl$)_2$-Si(OR)$_2$ or $(C_1-C_7$ alkyl)-Si(OR)$_3$, respectively, biotinylated forms thereof, or mixtures of the aforesaid, wherein each of the Rs independently is a $(C_1-C_4)$alkyl, preferably methyl or ethyl, and the $(C_1-C_7)$ alkyl group of the trialkoxysilane, or one or two of the $(C_1-C_7)$alkyl groups of the dialkoxysilane, is substituted at a terminal carbon atom with a functional group such as mercapto, amino, and hydroxyl; and the $(C_1-C_7)$alkyl group of the trialkoxysilane, or one or two of the $(C_1-C_7)$alkyl groups of the dialkoxysilane is optionally further interrupted with one or more —NH— groups.

The term "alkyl", as used herein, typically means a straight or branched hydrocarbon radical, wherein "$(C_1-C_7)$alkyl" and "$(C_1-C_4)$alkyl" particularly refer to such radicals having 1-7 or 1-4 carbon atoms, respectively. Non-limiting examples of such alkyls include methyl, ethyl, n-propyl, isopropyl, n-butyl, sec-butyl, isobutyl, tert-butyl, n-pentyl, 2,2-dimethylpropyl, n-hexyl, n-heptyl, and the like. The term "$(C_1-C_7)$ alkylene" refers to a straight or branched divalent hydrocarbon radical having 1-7 carbon atoms and include, e.g., methylene, ethylene, propylene, butylene, 2-methylpropylene, pentylene, 2-methylbutylene, hexylene, 2-methylpentylene, 3-methylpentylene, 2,3-dimethylbutylene, heptylene, and the like.

In certain particular embodiments, the alkoxysilane-based polymer is formed by polymerization of a mercapto-functional alkoxysilane of the general formula HS—$(C_1-C_7)$alkylene-SiR(OR)$_2$ or HS—$(C_1-C_7)$alkylene-Si(OR)$_3$, preferably HS—$(C_1-C_7)$alkylene-Si(OR)$_3$, a biotinylated form thereof, or a mixture of the aforesaid, wherein each of the Rs independently is a $(C_1-C_4)$alkyl, preferably methyl or ethyl. Non-limiting examples of mercapto-functional alkoxysilanes include mercaptomethylmethyldiethoxysilane [$(C_2H_5O)_2(CH_3)Si$—$CH_2$—SH], mercaptomethyl methyldimethoxysilane [$(CH_3O)_2(CH_3)Si$—$CH_2$—SH], 3-mercaptopropylmethyl diethoxysilane [$(C_2H_5O)_2(CH_3)Si$—$(CH_2)_3SH$], 3-mercaptopropylmethyl dimethoxysilane [$(CH_3O)_2(CH_3)Si$—$(CH_2)_3SH$], 3-mercaptopropyltrimethoxysilane (MPS) [$(CH_3O)_3Si$—$(CH_2)_3SH$], 3-mercaptopropyltriethoxysilane [$(C_2H_5O)_3Si$—$(CH_2)_3SH$], and biotinylated forms thereof.

In other particular embodiments, the alkoxysilane-based polymer is formed by polymerization of an amino-functional alkoxysilane of the general formula $H_2N$—$(C_1-C_7)$alkylene-SiR(OR)$_2$ or $H_2N$—$(C_1-C_7)$alkylene-Si(OR)$_3$, preferably $H_2N$—$(C_1-C_7)$alkylene-Si(OR)$_3$, a biotinylated form thereof, or a mixture of the aforesaid, wherein each of the Rs independently is a $(C_1-C_4)$alkyl, preferably methyl or ethyl, and the $C_1-C_7$ alkylene is optionally interrupted with one or more —NH— groups. Non-limiting examples of amino-functional alkoxysilanes include $N^1$-(3-(trimethoxysilyl)propyl)ethane-1,2-diamine [$(CH_3O)_3Si(CH_2)_3NH(CH_2)_2NH_2$], $N^1$-(3-(triethoxysilyl)propyl)ethane-1,2-diamine [$(CH_3CH_2O)_3Si(CH_2)_3NH(CH_2)_2NH_2$], 3-aminopropyltrimethoxysilane (APS) [$(CH_3O)_3Si(CH_2)_3NH_2$], 3-aminopropyl triethoxysilane [$(CH_3CH_2OO)_3$—$Si(CH_2)_3NH_2$], 4-aminobutyltriethoxysilane [$(CH_3CH_2O)_3$—$Si(CH_2)_4NH_2$], 4-aminobutyltrimethoxysilane [$(CH_3O)_3Si(CH_2)_4NH_2$], $N^1$-(3-(dimethoxy(methyl)silyl)-2-methylpropyl)ethane-1,2-diamine [$(CH_3O)_2(CH_3)Si$—$CH_2CH(CH_3)CH_2NH(CH_2)_2NH_2$], $N^1$-(3-(diethoxy(methyl)silyl)-2-methylpropyl)ethane-1,2-diamine [$(CH_3CH_2O)_2(CH_3)Si$—$CH_2CH(CH_3)CH_2NH(CH_2)_2NH_2$], aminopropylmethyldimethoxysilane [$(CH_3O)_2(CH_3)Si$—$(CH_2)_3NH_2$], aminopropylmethyldiethoxysilane [$(C_2H_5O)_2(CH_3)Si$—$(CH_2)_3NH_2$], and biotinylated forms thereof.

In further particular embodiments, the alkoxysilane-based polymer is formed by polymerization of a mixture of a mercapto-functional alkoxysilane, e.g., a mercapto-functional alkoxysilane of the general formula HS—$(C_1-C_7)$alkylene-SiR(OR)$_2$ or HS—$(C_1-C_7)$alkylene-Si(OR)$_3$, preferably HS—$(C_1-C_7)$alkylene-Si(OR)$_3$, a biotinylated form thereof, or a mixture of the aforesaid, as defined above; and an amino-functional alkoxysilane, e.g., an amino-functional alkoxysilane of the general formula $H_2N$—$(C_1-C_7)$alkylene-SiR(OR)$_2$ or $H_2N$—$(C_1-C_7)$alkylene-Si(OR)$_3$, preferably $H_2N$—$(C_1-C_7)$alkylene-Si(OR)$_3$, a biotinylated form thereof, or a mixture of the aforesaid, as defined above. In one specific such embodiment, the alkoxysilane-based polymer is formed by polymerization of a mixture of MPS and APS.

In one particular embodiment exemplified in the studies described herein (FIG. 1), the semiconductor device of the present invention is composed of a first insulating layer of undoped GaAlAs which is on top of a first conducting semiconductor layer of n-doped GaAs, said first conducting semiconductor layer is on top of a second insulating layer of undoped GaAlAs which is on top of a third insulating layer of undoped InGaAs, said third insulating layer is on top of a fourth insulating layer of GaAs, wherein on top of said first insulating layer is a second conducting semiconductor layer of GaAs on top of which is an upper conducting semiconductor layer of GaAs, and said protective layer is fabricated on top of said upper conducting semiconductor layer. In a more particular embodiment, the protective molecular layer of this semiconductor device comprises a polymer formed following polymerization of a mixture of MPS and APS.

In certain embodiments, the semiconductor device of the present invention comprises at least one insulating or semi-insulating layer each independently as defined above, at least one conducting semiconductor layer each independently as defined above, two conducting pads, a protective molecular layer as defined above, and said ligand or active site-containing protein directly linked to said protective molecular layer via a functional group of the alkoxysilane forming the protective molecular layer, e.g., an amino, mercapto, carboxyl or hydroxyl group of said alkoxysilane.

In other embodiments, the semiconductor device of the present invention comprises at least one insulating or semi-insulating layer each independently as defined above, at least one conducting semiconductor layer each independently as defined above, two conducting pads, a protective molecular layer as defined above, and said ligand or active site-containing protein indirectly linked to said protective molecular layer.

In certain particular such embodiments, said ligand or active site-containing protein is indirectly linked to said protective molecular layer via a mono- or bi-layer membrane comprising an amphiphilic compound or a mixture thereof, wherein said membrane is adhered to said protective molecular layer. In certain more particular such embodiments, said ligand or active site-containing protein is immobilized on, i.e., adsorbed to, or incorporated into, said mono- or bi-layer membrane, e.g., by linking to particular chemical groups in said membrane that are capable of forming strong non-covalent or covalent bonds with said ligand or active site-containing protein.

In other particular such embodiments, said ligand or active site-containing protein is indirectly linked to said protective molecular layer via a linker such as a ligand-binding protein, biotin, or a biotin-like molecule. In certain more particular such embodiments, said ligand or active site-containing protein is indirectly linked to said protective molecular layer via a ligand-binding protein. Examples of ligand-binding proteins include, without being limited to, Protein A, Protein G, avidin, streptavidin, and antibodies. The term "antibodies", as used herein, refers to polyclonal and monoclonal antibodies of avian, e.g. chicken, and mammals, including humans, and to fragments thereof such as F(ab')$_2$ fragments of polyclonal antibodies, and Fab fragments and single-chain Fv fragments of monoclonal antibodies. The term also refers to chimeric, humanized and dual-specific antibodies.

Biotin, also known as Vitamin H or coenzyme R, is a water-soluble B-complex vitamin (vitamin B$_7$) composed of a ureido (tetrahydroimidizalone) ring fused with a tetrahydrothiophene ring, wherein a valeric acid substituent is attached to one of the carbon atoms of the tetrahydrothiophene ring. The terms "biotin-like molecule" and "biotin-like residue" as used herein refer to any compound or a residue thereof, respectively, having a biotin-like structure, capable of binding to the tetrameric proteins avidin and streptavidin with a dissociation constant ($K_d$) similar to that of biotin, i.e., in the order of ~$10^{-15}$ M. Non-limiting examples of biotin-like molecules are diaminobiotin and desthiobiotin, as well as molecules comprising a tetrahydroimidizalone ring fused with a tetrahydrothiophene ring which is found in biotin, or analogs thereof such as those found in diaminobiotin and desthiobiotin.

The term "biotinylated form", as used herein with respect to the dialkoxysilanes, trialkoxysilanes or tetraalkoxysilanes forming the protective molecular layer, or the amphiphilic compounds forming the mono- or bi-layer membrane, refers to any of said alkoxysilanes or amphiphilic compounds, respectively, when covalently attached to a biotin residue or to a residue of a biotin-like molecule, e.g., via one of the functional groups thereof. Biotinylation of alkoxysilanes or amphiphilic compounds as defined above can be conducted using any technology or method commonly known in the art.

Protein A is a surface protein originally found in the cell wall of Staphylococcus aureus, capable of binding immunoglobulins. The protein is composed of five homologous Ig-binding domains that fold into a three-helix bundle, wherein each domain is capable of binding proteins from many of mammalian species, preferably IgGs. In particular, Protein A binds the heavy chain with the Fc region of most immunoglobulins and also within the Fab region in the case of the human VH3 family.

Protein G is an immunoglobulin-binding protein expressed in group C and G Streptococcal bacteria much like Protein A but with different specificities. It is a cell surface protein that is commonly used in purifying antibodies through its binding to the Fc region. Protein G in its natural form also binds albumin; however, because serum albumin is a major contaminant of antibody sources, the albumin binding site has been removed from recombinant forms of Protein G.

Avidin is a homotetrameric biotin-binding protein having four identical subunits, produced in the oviducts of birds, reptiles and amphibians deposited in the whites of their eggs. Each one of the subunits can bind to biotin with high affinity and specificity, wherein the $K_d$ of avidin is ~$10^{-15}$ M, making it one of the strongest known non-covalent bonds.

Streptavidin is a protein purified from Streptomyces avidinii. Streptavidin homo-tetramers have an extraordinarily high affinity for biotin, wherein its binding to biotin is one of the strongest non-covalent interactions known in nature.

The ligand or active site-containing protein may be indirectly linked to the protective molecular layer of the semiconductor device of the present invention via a mono- or bi-layer membrane comprising an amphiphilic compound or a mixture thereof, which is adhered to the protective molecular layer.

In certain embodiments, the amphiphilic compound comprised within said monolayer or bilayer membrane is a phospholipid, i.e., a lipid capable of forming a lipid bilayer, a biotinylated form thereof, or a mixture of the aforesaid. Such phospholipids may be either phosphoglycerides, also known as glycerophospholipid, or phosphosphingolipids.

Particular types of phosphoglycerides include, without being limited to, plasmalogens; phosphatidates, i.e., phosphatidic acids; phosphatidylethanolamines (cephalin); phosphatidylcholines (lecithin) such as egg phosphatidylcholin (EPC); phosphatidylserine; phospatidylinositol; phosphatidylinositol phosphate, i.e., phosphatidylinositol 3-phosphate, phosphatidylinositol 4-phosphate, or phosphatidylinositol 5-phosphate, phosphatidylinositol bisphosphate, and phosphatidylinositol triphosphate; glycolipids such as glyceroglycolipids, glycosphingolipids, and glycosylphosphatidylinopsitols; phosphatidyl sugars; and a biotinylated forms thereof such as dioleoyl-sn-glycero-3-phosphoethanolamine-N-(cap biotinyl) (BCPE), Biotin-Phosphatidylcholine (Cat. No. L-11B16, Echelon®), Biotin Phosphatidylinositol 3-phosphate (Cat. No. C-03B6, Echelon®), Biotin Phosphatidylinositol 4,5-bisphosphate (Cat. No. C-45B6, Echelon®), Biotinylated phosphatidylinositol 3,4,5-trisphosphate, and 1-((1-octanoyl-N'-biotinoyl-1,6-diaminohexane-2R-octanoyl)phosphatidyl)inositol-3,4,5-triphosphate, tetrasodium salt (PtdIns-(3,4,5)-P$_3$-biotin (sodium salt); Cayman, Chemical Item Number 10009531).

Examples of phosphosphingolipids include, without being limited to, ceramide phosphorylcholine, ceramide phosphorylethanolamine, ceramide phosphorylglycerol, and biotinylated forms thereof such as Biotin Sphingomyelin (Cat. No. S-400B, Echelon®).

The decision whether to link said ligand or active site-containing protein to said protective molecular layer via a lipid mono- or bi-layer membrane depends on the type and properties of said ligand or active site-containing protein, wherein formation of such a membrane might be preferred, e.g., in cases a membrane protein should be linked to the protective molecular layer as well as in order to avoid non-specific interactions of either or both of said ligand or active site-containing protein, and the analyte detected, i.e., said active site-containing protein or ligand, respectively, with said protective molecular layer.

In certain particular embodiments, the semiconductor device of the invention comprises at least one insulating or semi-insulating layer each independently as defined above, at least one conducting semiconductor layer each independently as defined above, two conducting pads, a protective molecular layer as defined above, and said ligand or active site-containing protein indirectly linked to said protective molecular layer via a mono- or bi-layer membrane comprising a mixture of an amphiphilic compound and a biotinylated form of an amphiphilic compound, wherein a biotinylated form of said ligand or active site-containing protein is non-covalently attached via an avidin or streptavidin molecule to the biotin or biotin-like residues in said mono- or bi-layer membrane.

In other particular embodiments, the semiconductor device of the invention comprises at least one insulating or semi-insulating layer each independently as defined above, at least one conducting semiconductor layer each independently as defined above, two conducting pads, a protective molecular layer as defined above, and said ligand or active site-containing protein indirectly linked to said protective molecular layer via biotin or a biotin-like molecule, wherein said biotin or biotin-like molecule is covalently linked to a functional group in said protective molecular layer, and a biotinylated form of said ligand or active site-containing protein is non-covalently attached via an avidin or streptavidin molecule to the biotin or biotin-like residues linked to said protective molecular layer.

In further particular embodiments, the semiconductor device of the invention comprises at least one insulating or semi-insulating layer each independently as defined above, at least one conducting semiconductor layer each independently as defined above, two conducting pads, a protective molecular layer as defined above, and said ligand or active site-containing protein indirectly linked to said protective molecular layer via a ligand binding protein such as Protein A, Protein G, streptavidin, avidin or an antibody, wherein said ligand binding protein is covalently linked to a functional group in said protective molecular layer, and non-covalently attached to said ligand or active site-containing protein.

Ligand binding proteins such as Protein A and Protein G can be used, e.g., when the active site-containing protein indirectly linked to the protective molecular layer is an antibody. Ligand binding proteins such as streptavidin and avidin can be used, e.g., to bind biotin or a biotin-like molecule, to which said ligand or active site-containing protein is linked. An antibody can be used as a ligand binding protein, e.g., when the active site-containing protein indirectly linked to the protective molecular layer is an antigen capable of forming strong interactions with said antibody.

The semiconductor device of the present invention may be used for the detection of an active site-containing protein or a ligand thereof in a solution. Said solution may be an aqueous solution, e.g., a physiological solution, a bodily fluid such as amniotic fluid, aqueous humour, vitreous humour, bile, blood serum, breast milk, cerebrospinal fluid, cerumen (earwax), endolymph, perilymph, female ejaculate, gastric juice, mucus, peritoneal fluid, saliva, sebum (skin oil), semen, sweat, tears, vaginal secretion, vomit and urine, or a bodily fluid-based solution, i.e., an aqueous solution in which a bodily fluid is dissolved.

In certain embodiments, the semiconductor device of the present invention, in any of the configurations defined above, is further used for quantification of said active site-containing protein or ligand thereof in said solution, wherein the current change through the semiconductor device when a constant electric potential is applied between the two conducting pads is proportional to the concentration of said active site-containing protein or ligand thereof in the solution.

GaAs/AlGaAs-based MOCSER devices as defined above were fabricated as described in detail in the Experimental section hereinafter. A protective molecular layer of MPS was fabricated on top of each one of the devices, and the thickness and quality of said layer, as well as the protection against etching provided thereby, were determined. In contrast to silicon oxide-coated GaAs-based MOCSERs, wherein a dramatic reduction in the sensitivity of the device was observed due to the elimination of the ability to modify the surface states on the GaAs, no reduction in the sensitivity of the MPS-protected GaAs MOCSERs was observed.

In one of the studies conducted, an active site-containing protein, more particularly, streptavidin or avidin, was bound to the protective molecular layer via a lipid bilayer membrane. In order to ensure adhesion of said bilayer membrane to the MPS-coated MOCSER, APS was first adsorbed on top of the MPS-coated GaAs devices.

The bilayer membrane was formed on the MPS-APS coated (modified) GaAs devices by the vesicle fusion method, using vesicles prepared from egg phosphatidylcholin (EPC); mixtures of EPC and 1,2-dioleoyl-sn-glycero-3-phosphoethanolamine-N-(lissamine rhodamine B sulfonyl) (LRBPE); and mixtures of EPC and 1,2-dioleoyl-sn-glycero-3-phosphoethanolamine-N-(cap biotinyl) (BCPE). Vesicles were prepared according to a known protocol, and were then sonicated and down-sized to either 100 or 50 nm, resulting in final vesicle-concentration of $3 \times 10^8/\mu l$. For membrane deposition, the MPS-APS coated device was inserted inside a flow system fixed on top of the sensing area of the device, and the mixtures of vesicles were injected into the flow cell either manually or using a peristaltic pump. After injection, the vesicles were incubated so as to allow fusion and spreading on the surface to form a lipid bilayer, unfused lipid excess was removed, and the smoothness and integrity of the bilayer membrane formed were observed.

The effect of vesicle size on the formation of a homogeneous bilayer membrane on the MPS-APS-modified GaAs substrate was evaluated using fluorescence imaging. As found, incubation of the EPC-LRBPE (99:1) vesicles on the MPS-APS-coated GaAs substrate, for 5 min, was sufficient for vesicle adhesion and rupture into a bilayer membrane; however, some vesicles remained unruptured, leading to a grainy fluorescence image. Longer incubation time increased the number of unruptured vesicles. Downsizing the EPC-LRBPE (99:1) vesicles from 100 to 50 nm dramatically decreased the number of unruptured vesicles on the MPS-APS-coated GaAs substrate, leading to a homogeneous image similar to that observed on hydrogen fluoride (HF)-etched glass slide. The membrane attachment to the MPS-coated GaAs devices in the presence of APS was improved compared to that in the absence of APS. The effect of vesicle size on the formation of a homogeneous bilayer membrane on the MPS-APS-coated MOCSER substrate was also evaluated using AFM-surface-analysis measurement. The root mean square roughness value of the ~25 nm MPS-APS-coated GaAs devices was found to be ~1.6 nm. The MPS polymer was not homogeneous and contained some holes varying from 5 nm to 120 nm in diameter, sufficient to trap a single 100 nm vesicle, preventing its attachment to nearby vesicles and therefore its rupture owing to lack of certain surface density of vesicles. By downsizing the vesicle size from 100 to 50 nm, the possibility of two vesicles to adsorb to the same hole was increased, leading to their rupture into a homogeneous bilayer membrane.

The stability and integrity of the bilayer membrane formed over time were compared to those of a similar membrane formed on HF-etched glass. As found, while integrity of the membrane adsorbed on glass slide was stable for more than 7 days in the presence of 2 mM CaCl$_2$, integrity of the membrane adsorbed on the MPS-APS-modified GaAs substrate deteriorated after ~5 days.

After forming a membrane of 50 nm EPC-BCPE vesicles on the MPS-APS-coated MOCSER devices, a solution containing either streptavidin or avidin was added to the biotinylated membrane, allowed to interact with the biotin molecules in the BCPE, and was then washed; and streptavidin or avidin attachment to the EPC-BCPE membrane was evaluated.

In another study conducted, an active site-containing protein, more particularly, sheep anti-human hemoglobin antibody, was bound to the protective molecular layer by immobilizing said antibody on the protective molecular layer surface via Protein G, acting as a ligand binding protein, and blocking the non-binding sites by bovine serum albumin (BSA). In order to enable binding biological molecules to the protective molecular layer, APS was adsorbed on top of the MPS-coated GaAs devices.

The change in the current of the MOCSER after sequentially adsorbing Protein G, BSA and anti-human hemoglobin antibodies was tested, and as found, the net change in current was negative when Protein G was introduced into the sensing area; positive upon introducing of BSA; and negative during anti-human hemoglobin antibodies interaction with the surface of the device. Since Protein G, BSA, and sheep anti-human hemoglobin antibodies are all negatively charged protein molecules at pH 7.4, these results demonstrate that the sensing mechanism of the MOCSER is different from most generally accepted capacitive theory applicable for ISFETs.

Example 1 hereinafter describes a study in which the response of a biotinylated lipid bilayer membrane (an EPC-BCPE membrane containing a fraction of ~20% biotin)-coated MPS-APS modified GaAs device to phosphate buffer solutions containing various analytes was tested. Analytes dissolved in phosphate buffer solution were injected sequentially into a flow cell fixed on top of the sensing area of the device, and phosphate buffer solution was injected between the analytes for washing and removing analyte excess. A constant potential of 1.0 V was applied between source and drain of the device, and changes in source-drain current were monitored as function of time. An Ag/AgCl pseudo reference electrode was placed in a sealed tube and connected via a salt bridge to maintain a stable and constant potential over the surface of the device.

As shown in this Example, whereas the source-drain current response to pH change was immediate, stable, and linear within the pH range studied, the changes in the current observed in the bilayer membrane-coated device when exposed to various concentrations of negatively- or positively-charged amino acids at pH=7, exemplified by L-glutamic acid or L-lysine, respectively, were correlated with the analyte concentration. In particular, while the current increased as the concentration of L-glutamic acid increased, it decreased with increasing L-lysine concentration. The detection thresholds for L-lysine and L-glutamic acid in the presence of EPC membrane were about 12.5 mM and 6.2 mM, respectively, and they improved to 3.2 mM and 1.6 mM for L-lysine and L-glutamic acid, respectively, in the absence of the bilayer membrane, indicating that said membrane reduces the sensitivity of the device by about a factor of four.

Exposing the biotinylated membrane to either streptavidin that is negatively charged at neutral pH, or avidin that is positively charged at neutral pH, at concentrations above 0.8 µM at pH=7, resulted in a significant change in the MOCSER source-drain current. In particular, the current increased as the streptavidin concentration increased, but remained constant when the solution was changed to buffer with no streptavidin, indicating a strong (and seemingly irreversible on the time scale of the experiment) binding of the streptavidin to the biotin. When exposed to avidin, the current through the MOCSER was reduced. When an EPC-based membrane without biotin was exposed to the same solution, a change in the current was observed; however, this change could be completely reversed by washing with buffer.

Changes in the source-drain current were observed when devices to which streptavidin was initially attached were exposed to rabbit anti-streptavidin antibody in serum. As shown, the current decreased upon exposure to the antibodies at concentrations of 0.031, 0.125 and 1 mg/ml, indicating strong and seemingly irreversible binding of the anti-streptavidin molecules to the biotin-streptavidin complexes, wherein the signal is accumulating as a function of the amount of analyte to which the sensor is exposed. As shown in a control experiment, when devices comprising an EPC-based membrane without biotin were exposed to the same antibody containing-serum solution, small positive offset in the current was observed upon washing, indicating non-specific binding of serum species to the membrane.

The study described in Example 1 demonstrates the sensing of various species that interact differently with the bilayer membrane-coated MOCSER. In the case of pH and amino acids sensing, the interaction of the analytes with the substrate is weak, as validated by the ability to remove the analyte from the sensor by washing with the buffer solution. The dependence of the signal on the analyte concentration in these cases is complicated since it reflects the change in the bilayer charge and the extent that this change affects the charge on the MOCSER surface itself. Importantly, since the molecules forming the membrane are zwitterions, no preference, in terms of the interaction strength, was observed in the two oppositely charged amino acids.

Much of the efforts in developing new diagnostic tools are shifting from disease diagnostics to disease management (Coughlin et al., 2006). This means that point of care (POC) sensors will play an important role in helping controlling the patient condition and in evaluating specific medical treatment. These sensors should be easy to handle and cost effective (Price, 2001; Pflfflin and Schleicher, 2008; Makowski and Ivanisevic, 2011). Diseases associated with hemoglobin like anemia, diabetes (Mayer and Freedman, 1983), hematemesis (Ian et al., 2008), hematuria (Landefeld and Beyth, 1993), and hemoglobiuria (Rother, 2005) need continuous monitoring of the hemoglobin over prolong period of time. Most of the present available POC devices for sensing hemoglobin use traducers based on amperometric, colorimetric and piezoelectric techniques (McMurdy et al., 2008; Park et al., 2005) and the most popular are the electrode-based sensors which operate on amperometric potential principles. The major drawback of this technique is that the devices lose the sensitivity due to over potential applied (Salimi et al., 2005).

Hematuria and hemoglobiuria are diseases associated with hemoglobin and needs continue monitoring of hemoglobin in urine as they are symptoms for kidney stones or renal cancer etc (Mayer and Freedman, 1983; Ian et al., 2008; Rother, 2005). Common clinical practices for sensing hemoglobin are by ELISA or dipstick techniques. ELISA provides quantitative results; however, the response time is very long (on hours scale), it requires expert technician, and specialized equipment which is both bulky and relatively expensive (Lazcka et al., 2007). The dip stick sensor is simple to use and inexpensive; however, it provides qualitative information only (Messing, 2007).

Example 2 describes a study in which the response of the MPS-APS modified GaAs MOCSER, wherein sheep anti-human hemoglobin antibodies were linked to the protective molecular layer via Protein G, to human hemoglobin dissolved in either phosphate buffer solution or urine was tested. The experimental setup in this study was similar to that described above. Analytes dissolved in either phosphate buffer solution or urine were injected sequentially into the flow cell, and either phosphate buffer solution or urine was injected between the analytes for washing and removing analyte excess.

As shown in this Example, the response of the MPS-APS modified GaAs device, in which sheep anti-human hemoglobin antibodies were linked to the protective molecular layer via Protein G, to human hemoglobin dissolved in either phosphate buffer solution or urine, was immediate and stable. The current measured in the MOCSER decreased when hemoglobin interacted with the anti-hemoglobin antibodies linked to the MPS-APS-modified surface, and recovered after washing with the phosphate buffer or urine, wherein the signal was correlated with the concentration of the analyte molecules. The sensitivity of the device to hemoglobin based on the experiments conducted was 10 μg/ml and 100 μg/ml of hemoglobin in phosphate buffer and urine, respectively. The sensitivity of the device to hemoglobin in urine was lower than in phosphate buffer, probably as the urine salt concentration is much higher.

In order to verify the selectivity of the MOCSER, the source-drain current in response to hemoglobin solutions in both phosphate buffer and urine, when sheep anti-human hemoglobin antibodies were not immobilized on the gate area, and the surface was only functionalized with protein G and BSA, was measured. As found, no response to the hemoglobin analytes was observed, indicating the high selectivity of the device. When analytes containing avidin, representing a non-specific antigen, were introduced to a MOCSER having a gate area on which sheep anti-human hemoglobin antibodies were immobilized, no change in the current was observed demonstrating the high specificity of the device.

The operation of the MOCSER as a sensor is based on the fact that it is capacitance sensitive (Ghafar-Zadeh et al., 2010). Thus, when the device is immersed in electrolyte solution with a reference electrode, a double layer is formed on its surface. Clearly, when the analyte on the surface of the membrane is negatively charged, the charge accumulating on the surface of the device is positive and vice versa. Since the device is based on n-doped GaAs, positive charge on the surface increases the charge carrier concentration in the conductive channel and the source-drain current increases. The opposite is true for negative charge on the surface of the GaAs that causes depletion in the charge carrier concentration and hence reduction in the source-drain current.

The amount of charge accumulating on the surface of the GaAs per charge on the analyte depends on the potential, V, built between the surface of the membrane and the GaAs surface which is given by: $V \propto Qd/\in$, where Q is the charge per surface area of the analyte, d is the thickness of the MPS-APS-membrane layer, and $\in \approx 2$ is the electric permittivity of this layer. Since most of the thickness is due to the MPS layer, its value is about the same for a system with or without the membrane. Hence, the difference between the response curves obtained with and without a membrane stems from increase of $\in$ upon coating the device with the membrane. This increase can be due to a thin water layer located between the membrane and the APS layer.

The MOCSER is different from the well-developed ion selective-FET (ISFET) (Mckinley et al., 1984; Fogt et al., 1985), where the gate on the transistor is replaced with ion selective membrane that allows specific ions to penetrate, and these ions define the electric potential on the gate. It is also different from the regular chemical field-effect transistor (ChemFET) or insulated gate field-effect transistor (IGFET) where the metal gate terminal is coated with molecules that interact with a specific analyte (Lee et al., 2009). In these cases, the detection is performed by monitoring the change in the gate potential required for maintaining a constant current.

In the present device, the current through the device for a given source-drain potential is determined by the resistivity which is controlled by the band bending in the semiconductor: The more bent the bands, the lower the current. In general, the band bending is determined by the charge on the surface states. Hence, the sensitivity of the device stems from the change induced in the surface states charge. The density of surface states of GaAs is of ~$10^3$ states/cm$^2$, and it has been shown that a change of about 1% in this charge is enough to affect the current in a detectable way (Capua et al., 2009a). The Dipole moment that would result from this charge reorganization would have very little effect on the surface potential and would not be felt by the MOCSER (Naaman, 2011). Hence, the surface states are the source of sensitivity of the current sensor, a sensitivity exceeding what can be obtained by modifying the voltage on a metal gate.

The approach presented herein, in which chemical interaction occurring on the outer side of the membrane, if present, or the protective molecular layer is transformed into an electric signal changing the current measured in the MOCSER can be implemented for studying protein-membrane and protein-protein interactions and kinetics.

In summary, the transmission of information through the lipid mono- or bi-layer membrane, if present, or through the protective molecular layer, on the semiconductor device of the present invention does not involve charge/mass transfer, but rather relies on the ability of adsorbed organic molecules to control electronic devices. More particularly, the operation of this semiconductor is based on variation in the electrochemical potential on the surface of a GaAs FET-like structure, in which the gate area is covered by chemically adsorbed molecules. As shown herein, the special sensitivity of the MOCSER stems from the ability to modify the properties of the surface states located on the surface of the device. When the adsorbed molecules interact with other species, the energetics of the surface state is modified, affecting the electrochemical potential on the surface and as a result the source to drain current of the device.

In another aspect, the present invention thus provides a method for detection of an active site-containing protein or a ligand thereof in a solution, e.g., an aqueous solution such as a physiological solution, a bodily fluid, or a bodily fluid-based solution, said method comprising:

(i) exposing a semiconductor device as defined above to said solution; and (ii) monitoring the presence of said active site-containing protein or ligand in said solution according to the changes in the current measured in said semiconductor device when a constant electric potential is applied between the two conducting pads.

In one particular such aspect, the present invention provides a method for detection of said active site-containing protein in said solution, wherein the semiconductor device exposed to said solution in step (i) comprises said ligand linked either directly or indirectly to said protective molecular layer, and exposure of said ligand to a solution containing said active site-containing protein causes a current change through the semiconductor device when a constant electric potential is applied between the two conducting pads.

In another particular such aspect, the present invention provides a method for detection of said ligand in said solution, wherein the semiconductor device exposed to said solution in step (i) comprises said active site-containing protein linked either directly or indirectly to said protective molecular layer, and exposure of said active site-containing protein to a solution containing said ligand causes a current change through the semiconductor device when a constant electric potential is applied between the two conducting pads.

In view of the capabilities of the semiconductor device of the invention, in certain embodiments, the method of the present invention may further be used for quantification of said active site-containing protein or ligand thereof in the solution, wherein the current change through the semiconductor device when a constant electric potential is applied between the two conducting pads is proportional to the concentration of said active site-containing protein or ligand thereof in the solution.

The method of the invention may be used, e.g., for studying receptor-ligand pair interactions, more particularly, for monitoring the interaction of a receptor in a solution with a ligand directly or indirectly linked, as defined above, to the protective molecular layer, or vice versa.

In certain embodiments, the active site-containing protein and ligand thereof according to the method of the invention are an antibody and an antigen, e.g., a protein antigen, respectively, or vice versa. In certain particular embodiments, the semiconductor device used according to this method comprises said antibody linked either directly or indirectly to said protective molecular layer, and the method is used for selective detection and optionally quantification of said antigen in a solution. In other particular embodiments, the semiconductor device used comprises said antigen linked either directly or indirectly to said protective molecular layer, and the method is used for selective detection and optionally quantification of said antibody in a solution. According to the method of the invention, exposure of said antibody or antigen to a solution containing said antigen or antibody, respectively, causes a current change through the semiconductor device when a constant electric potential is applied between the two conducting pads. In particular such embodiments, the current change through the semiconductor device is proportional to the concentration of said antigen or antibody in the solution.

In other embodiments, the active site-containing protein and ligand thereof according to the method of the invention are an enzyme and either a substrate or inhibitor thereof, respectively, or vice versa. In certain particular embodiments, the semiconductor device used according to this method comprises said enzyme linked either directly or indirectly to said protective molecular layer, and the method is used for selective detection and optionally quantification of said substrate or inhibitor in a solution. In other particular embodiments, the semiconductor device used comprises said substrate or inhibitor linked either directly or indirectly to said protective molecular layer, and the method is used for selective detection and optionally quantification of said enzyme in a solution. According to the method of the invention, exposure of said enzyme or either substrate or inhibitor to a solution containing either said substrate or inhibitor or said enzyme, respectively, causes a current change through the semiconductor device when a constant electric potential is applied between the two conducting pads. In particular such embodiments, the current change through the semiconductor device is proportional to the concentration of said substrate or inhibitor or said enzyme in the solution.

In further embodiments, the active site-containing protein and ligand thereof according to the method of the invention are a receptor and either a protein or organic molecule, respectively, or vice versa. In certain particular embodiments, the semiconductor device used according to this method comprises said receptor linked either directly or indirectly to said protective molecular layer, and the method is used for selective detection and optionally quantification of said protein or organic molecule in a solution. In other particular embodiments, the semiconductor device used comprises said protein or organic molecule linked either directly or indirectly to said protective molecular layer, and the method is used for selective detection and optionally quantification of said receptor in a solution. According to the method of the invention, exposure of said receptor or either protein or organic molecule, to a solution containing either said protein or organic molecule or said receptor, respectively, causes a current change through the semiconductor device when a constant electric potential is applied between the two conducting pads. In particular such embodiments, the current change through the semiconductor device is proportional to the concentration of said protein or organic molecule or said receptor in the solution.

In still further embodiments, the active site-containing protein and ligand thereof according to the method of the invention are a lectin and a sugar, respectively. In certain particular embodiments, the semiconductor device used according to this method comprises said lectin, and the method is used for selective detection and optionally quantification of said sugar in a solution. In other particular embodiments, the semiconductor device used comprises said sugar, and the method is used for selective detection and optionally quantification of said lectin in a solution. According to the method of the invention, exposure of said lectin or sugar to a solution containing said sugar or lectin, respectively, causes a current change through the semiconductor device when a constant electric potential is applied between the two conducting pads. In particular such embodiments, the current change through the semiconductor device is proportional to the concentration of said sugar or lectin in the solution.

In certain particular embodiments, the method of the invention is used for detection and optionally quantification of hemoglobin or a degradation product thereof in a bodily fluid such as urine or in a bodily fluid-based solution, and the semiconductor device exposed to said bodily fluid or bodily fluid-based solution comprises an antibody to said hemoglobin or degradation product thereof linked either directly or indirectly to the protective molecular layer.

In other particular embodiments, the method of the invention is used for detection and optionally quantification of a specific protein in a bodily fluid or a bodily fluid-based solution, e.g., blood, plasma, urine, saliva, and gastro related solutions, and the semiconductor device exposed to said bodily fluid or bodily fluid-based solution comprises an antibody to said specific protein linked either directly or indirectly to said protective molecular layer.

The invention will now be illustrated by the following non-limiting Examples.

EXAMPLES

Experimental

Molecular Controlled Semiconductor Resistor (MOCSER) Fabrication

GaAs/AlGaAs MOCSER devices with a 600 μm long and 200 μm wide conducting channel were fabricated in a standard clean-room by photolithography techniques based on a pseudomorphic High Electron Mobility Transistor (pHEMT) structure (FIG. 1). Each fabricated chip contained 16 channels separated by 200 µm to minimize cross talking and leakage current. All the channels were electrically characterized before the measurements, and 4 out of the 16 channels were selected and measured simultaneously.

GaAs Corrosion Protection Using 3-Mercaptopropyltrimethoxysilane (MPS)

Since GaAs is used in an aqueous environment where it is susceptible to etching, a protective layer of MPS was fabricated on top of each device according to a common procedure (Kirchner et al., 2002). GaAs and GaAs/AlGaAs samples were cleaned in isopropanol, acetone, and ethanol for 10 min each, followed by UV/ozone oxidation for 10 min. In order to remove oxide layer and to expose the arsenic rich surface, the substrates were etched in 2% HF for 5 sec, washed in deionized water (DDW), etched in $NH_4OH$ (25% $NH_3$) for 30 sec, and washed in DDW again. Immediately after etching, the substrates were dried in nitrogen and immersed in 15 mM solution of MPS in ethanol at 50° C. for 4 hr. Polymerization of MPS was initiated by adding 3% (volume) of $NH_4OH$ (25%), after which the solution was kept at 50° C. for additional 16 hr. The samples were then rinsed with ethanol and dried under a stream of nitrogen. The thickness of the MPS layer was verified by ellipsometry (J. A. Woollam, model M-2000V) measurements within a range of 399-1000 nm, and estimated to be consistently in a range of 25-30 nm.

Figure 2A:
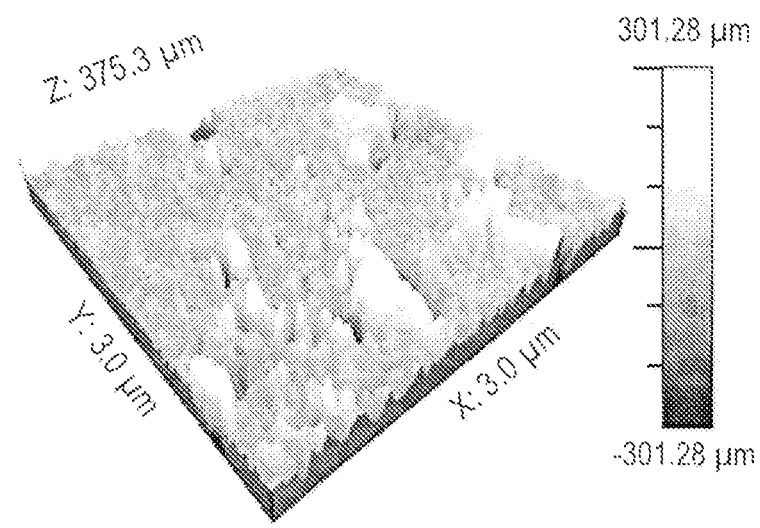
FIGS. 2A-2B show atomic force microscopy (AFM) images showing the effect of water exposure on a bare-GaAs surface (2A) and on a GaAs surface covered by ~25 nm MPS layer (2B).
Figure 2B:
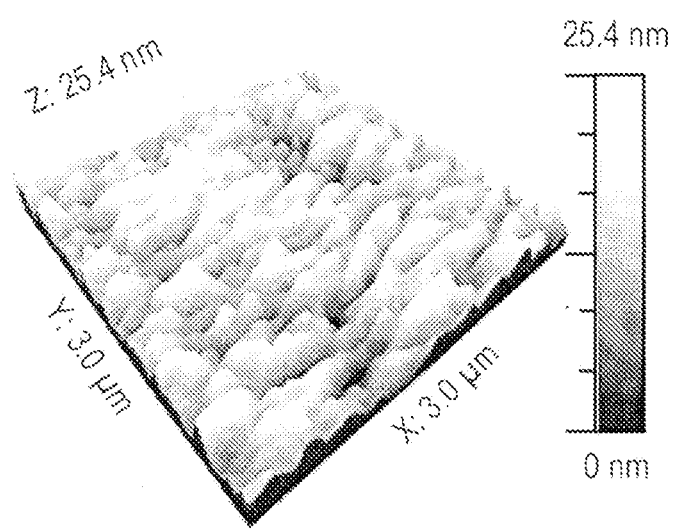

Corrosion protection was evaluated by means of atomic force microscopy (AFM) surface-analysis measurements (BioScope AFM, Veeco Metrology LLC, Santa Barbara, Calif.) on GaAs samples with and without MPS layer immersed in water for 24 hr. AFM images were acquired in tapping mode in water at room temperature (23-25° C.) using BioScope AFM with Nanoscope IV controller equipped with a large (G) scanner. As shown in FIG. 2, in the absence of MPS, the water molecules dissolved the oxides formed at the bare GaAs surface, resulting in continuous etching of the GaAs substrate; and the ensuing surface roughness was of the order of tens of µm (FIG. 2A). However, in case of GaAs substrates protected by MPS, no significant etching was observed and the roughness was the same as that of the GaAs wafer before etching, on the order of nanometers (FIG. 2B).

Images of 3×3 µm scan size were recorded using oxide-sharpened microfabricated $Si_3N_4$ cantilevers (DNP-S, Veeco Metrology, Santa Barbara, Calif.) with a nominal spring constant of ~0.12 N/m (as specified by the manufacturer) at scan rates of 1-3 Hz. Three types of images were acquired simultaneously: topography, amplitude and phase. The typical target amplitude was 300 mV (~22 nm) and set point was 230-240 mV (~17 nm) for all measurements. Image analysis was performed using WSxM 5.0 Develop 1.2 software (Schoning and Poghossian, 2002).

In contrast to silicon oxide-coated GaAs-based MOCSERs, wherein a dramatic reduction in the sensitivity of the device was observed due to the elimination of the ability to modify the surface states on the GaAs, no reduction was observed in the sensitivity of the MPS-protected GaAs-based MOCSERs.

In a further experiment, MPS solutions of 3 µl MPS in 1 ml EtOH or 4 µl MPS in 1 ml EtOH were used. First layer adsorbed for 4 hours, and after adding $NH_4OH$, polymerization starts and continued for 16 hours. AFM images taken support the conclusion that the quality of the primary layer depends on both the concentration of the adsorption solution and the time of deposition. Increasing deposition time from 4 to 8 hours significantly reduced the roughness of the surface, while further increasing the deposition time did not add to the surface smoothness. MPS solutions with concentrations of 3 or 4 µl MPS in 1 ml EtOH result in a continuous thin polymer layer with no pinholes.

Membrane Formation on MPS-Coated GaAs Devices

The bilayer membrane was formed on the MPS-coated GaAs devices by the vesicle fusion method (Richter et al., 2006; Wong et al., 1999; Sackmann, 1996), using the following lipids: egg phosphatidylcholin (EPC); 1,2-dioleoyl-sn-glycero-3-phosphoethanolamine-N-(lissamine rhodamine B sulfonyl) (LRBPE); and 1,2-dioleoyl-sn-glycero-3-phosphoethanolamine-N-(cap biotinyl) (BCPE).

Vesicles were prepared according to a protocol described by Barenholz et al. (1977) and Boukobza et al. (2001). Individual EPC lipids, mixtures of EPC-LRBPE (99:1, molar ratio), or mixtures of EPC-BCPE (8:2, molar ratio) were first diluted in tert-butyl alcohol and then lyophilized to remove all traces of organic solvent. The dry phospholipids were rehydrated by phosphate buffer containing 2 mM $CaCl_2$ (5 mg lipid in 450 µl of buffer 0.05 M, pH 7.0), creating multilamellar vesicles. In order to form unilamellar vesicles, the mixture was sonicated for 10 min using a Heat System Sonifier. Following sonication, vesicles were down-sized to 100 nm by extruding repetitively (39 times) through a polycarbonate film with 100 nm pores (Anatop™, Whatman) or to 50 nm by additional extrusion (39 times) through a polycarbonate film with 25 nm pores (Anatop™, Whatman). Vesicle size-distribution was measured using dynamic light scattering size-measurement (Viscotek 802 DLS, Malvern Instruments, Worcestershire, UK) and was found to be about 10% in a typical preparation. Final vesicle-concentration was $3 \times 10^8$/µl. Although vesicles were found to be stable for several days in phosphate buffer (0.05 M, pH 7.0), all vesicles were used immediately after preparation.

The characterization of the membrane formation was performed on GaAs substrate and not on the device itself. In order to ensure the adhesion of the bilayer membrane to the MPS-coated MOCSER, APS was adsorbed on top of the MPS-coated GaAs and GaAs/AlGaAs samples by overnight evaporation inside a sealed Petri dish at room temperature. Next, a flow cell was constructed on the surface of the MPS-APS-modified GaAs samples by attaching the HF-etched glass slide to the GaAs substrate with double-sided tape. For comparison, a bilayer membrane was formed on an HF-etched glass slide as well, on which a flow cell made of two HF-etched glass slides was constructed in a similar way. Solutions of 50 nm or 100 nm EPC-vesicles, mixtures of 50 nm or 100 nm EPC-LRBPE (99:1) vesicles, or mixtures of 50 nm EPC-BCPE (8:2) vesicles were injected into the flow cell and incubated for various time periods (from 5 min to 24 hr) in order to allow fusion and spreading on the sample surface to form a lipid bilayer. After incubation, the cell was rinsed with a phosphate buffer (0.05 M, pH 7.0) to remove unfused-lipid excess.

The smoothness and integrity of the supported bilayer formed on the MPS-APS-modified GaAs substrate were observed both by BioScope-AFM-surface-analysis measurement using 50 and 100 nm EPC-vesicles, and by fluorescence microscopy (Inverted microscope 1×70, Olympus, objective ×40) using 50 and 100 nm of fluorescently labeled EPC-LRBPE (99:1) mixture. AFM images of the lipid bilayers were acquired in tapping mode in a phosphate buffer solution (0.05 M, pH 7.0), at room temperature (23-25° C.). The typical target amplitude was 300 mV (~22 nm) and set point was 230-240 mV (~17 nm) for all measurements. Therefore, a "light" tapping was applied to avoid a possible damage to the membranes and influence of the scanning itself on the membrane state. Image analysis performed using WSxM 5.0 Develop 1.2 software (Schoning and Poghossian, 2002).

Figure 3:
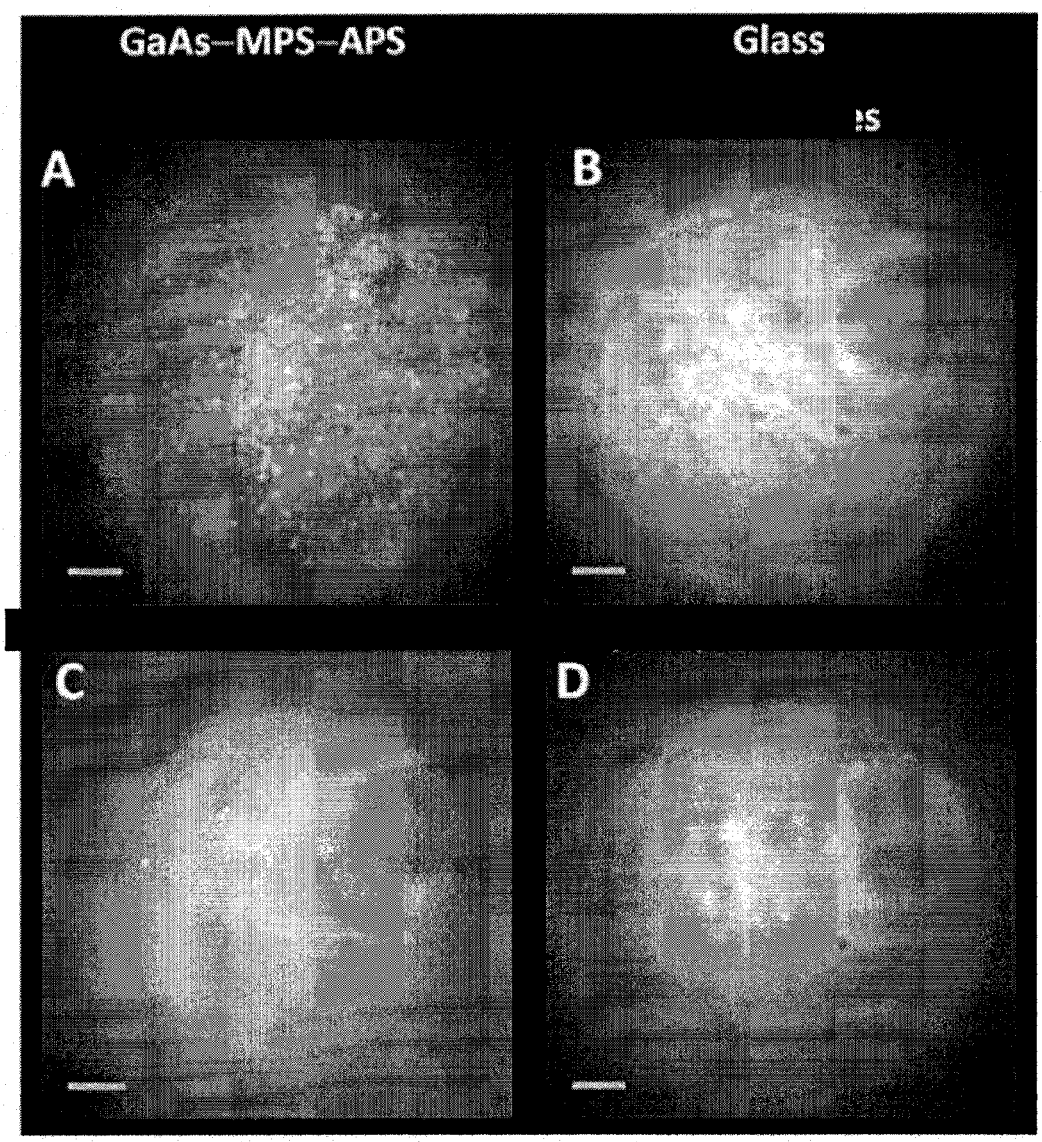
FIG. 3 shows fluorescence images of an MPS-APS modified GaAs surface and a glass slide (etched in HF) after exposure to 50 nm or 100 nm EPC-LRBPE (99:1) vesicle-containing solutions and incubation for 5 min. Indication for unruptured vesicles were observed on the MPS-APS-modified GaAs substrates when 100 nm EPC-LRBPE (99:1) vesicles were used (panel A), while the same vesicles formed a bilayer membrane on a glass slide, manifested as a much more uniform fluorescence distribution (panel B). Using smaller EPC-LRBPE (99:1) vesicles (50 nm) led to a uniform bilayer membrane formation on both MPS-APS-modified GaAs substrates (panel C) and glass slides (panel D). Scale bar: 35 μm.

Fluorescence imaging of the obtained bilayers indicates that in order to obtain a homogeneous surface coverage of the MPS-APS-modified GaAs substrates, 50 nm vesicles should be used (FIG. 3, panels A, C). This is in contrast to the case of HF-etched glass slide where 100 nm vesicle size is enough for uniform membrane formation (FIG. 3, panels B, D). The surfaces were illuminated with 532 nm light. It is well known that unilamellar lipid vesicles can fuse and spread on surfaces such as glass to form homogeneous surface coverage of a lipid bilayer (Boukobza et al., 2001). Hence, we could compare the results on glass with those on MPS-APS-modified GaAs substrate. When the vesicles on the surface were unruptured, the fluorescence image was non-homogeneous and looked grainy (FIG. 3, panel A). The image looks smooth when the sample is illuminated with a 532 nm beam in the absence of the vesicles. As further found, incubation of the EPC-LRBPE (99:1) vesicles on the MPS-APS-modified GaAs substrate, for 5 min, was sufficient for vesicle adhesion and rupture into a bilayer membrane. However, some vesicles remained unruptured, leading to a grainy fluorescence image. Longer incubation time prior to washing with phosphate buffer increases the number of unruptured vesicles. Downsizing the EPC-LRBPE (99:1) vesicles from 100 to 50 nm dramatically decreased the number of unruptured vesicles on the MPS-APS-coated GaAs substrate, leading to a homogeneous image similar to that observed on an HF-etched glass slide (FIG. 3, panel C). The membrane attachment to the MPS-coated GaAs devices in the presence of APS was improved compared to that in the absence of APS (data not shown).

Figure 4:
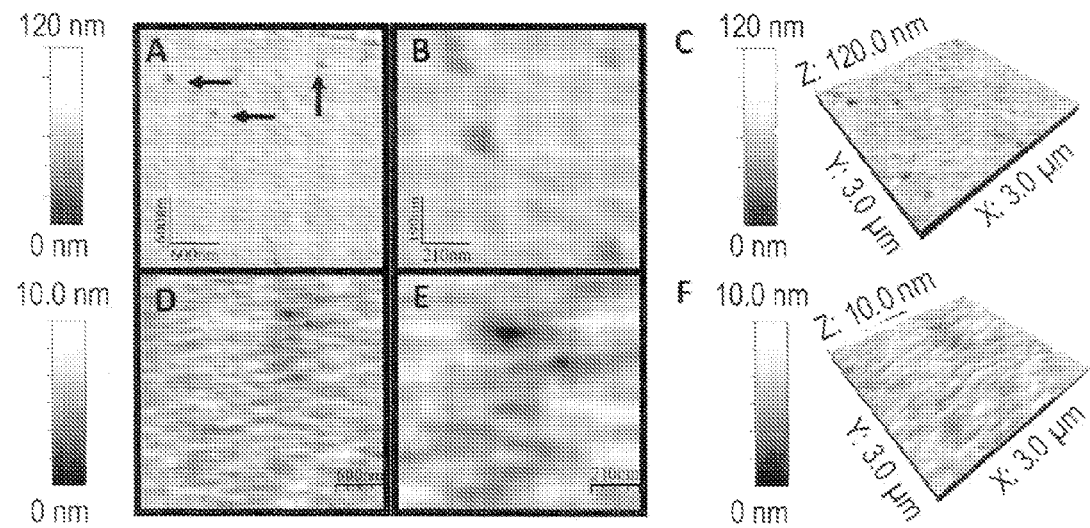
FIG. 4 shows the effect of vesicle size on vesicle rupture when adsorbed on ~25-nm MPS-APS-modified GaAs devices, observed by 2D- and 3D-AFM surface-analysis measurements. 100-nm EPC vesicles (marked by black arrows) were trapped in ~100-120 nm holes within the MPS polymer, preventing them from attaching to nearby vesicles and from their rupture (panels A-C). Downsizing the EPC vesicles from 100 nm to 50 mm increased the possibility of two vesicles to adsorb to the same hole, leading to their rupture into a homogeneous bilayer membrane formation (panels D-F).

The effect of vesicle size on the formation of a homogeneous bilayer on the MPS-APS-modified GaAs MOCSER substrate was also evaluated using AFM-surface-analysis measurement as shown in FIG. 4. The root mean square roughness value of the ~25 nm MPS-APS-modified GaAs devices was found to be ~1.6 nm. The MPS polymer was not homogeneous and contained some holes varying from 5 nm to 120 nm in diameter, sufficient to trap a single 100 nm vesicle, preventing its attachment to nearby vesicles and therefore its rupture owing to lack of certain surface density of vesicles (Chai et al., 2002). By downsizing the vesicle size from 100 to 50 nm, the possibility of two vesicles to adsorb to the same hole was increased, leading to their rupture into a homogeneous bilayer (Richter et al., 2006).

The stability and integrity of a membrane formed on MPS-APS-modified GaAs substrate over time were compared to those of a membrane formed on a glass, using fluorescence imaging. While integrity of the membrane adsorbed on HF-etched glass slide was stable for more than 7 days in the presence of 2 mM $CaCl_2$, integrity of the membrane adsorbed on the MPS-APS-modified GaAs substrate deteriorated after ~5 days (data not shown).

The results presented above show that GaAs device can be coated with a protecting layer of MPS and that a uniform membrane can be formed on top of an MPS-APS-modified GaAs device.

Streptavidin Attachment to EPC-BCPE (8:2)-Based Membranes

Streptavidin attachment to EPC-BCPE (8:2) membranes was confirmed by BioScope-AFM-surface-analysis measurements as described above. For this purpose, a flow cell was constructed on the surface of MPS-APS-modified GaAs samples by attaching HF-etched glass slide with double-sided tape. First, a lipid bilayer membrane was formed on MPS-APS-modified GaAs samples by incubating 50 nm EPC-BCPE (8:2) vesicles as described above. Next, 1 mg/ml streptavidin solution in phosphate buffer (0.05 M, pH 7.0) was added to the system, allowed to interact with the biotin molecules for 5 min so as to form biotin-streptavidin complex on top of the biotinylated membrane, and was then rinsed with phosphate buffer. In some experiments, 50 nm EPC-BCPE (498:1) vesicles (at a vesicle concentration of $3 \times 10^8/\mu l$) were added and allowed to interact for 5 min with the surface-adsorbed streptavidin molecules, and were then rinsed with phosphate buffer.

Anti-Hemoglobin Antibodies Attachment to MPS-APS-Modified MOCSER Surface

Figure 5:
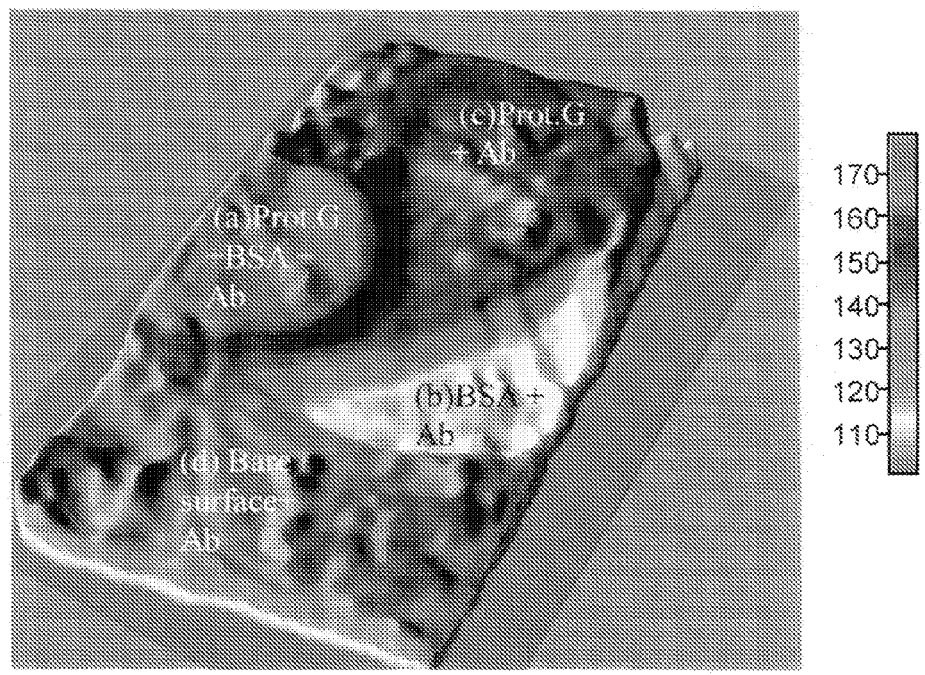
FIG. 5 shows a 3D fluorescence image of MPS-APS modified GaAs surface. Using spotting technique, the surface was modified at different regions with Protein G (Prot. G), BSA, and fluorescent tagged sheep anti-human hemoglobin antibodies (Ab). The highest Ab adsorption was observed when the surface was modified with Protein G and non-binding sites were blocked with BSA (a). Ab adsorption was low when the surface is bare (d) or modified with Protein G only (c), and almost no Ab adsorption was observed when the surface was modified with BSA only (b), demonstrating the blocking ability of BSA. This image further shows the depth profile indicating the number of molecular layers constructed.

Since protein adsorption on confined surfaces is complicated, the GaAs surface was first modified by adsorption of MPS-APS layers as defined above. Anti-human hemoglobin antibodies attachment to the MPS-APS-modified surface was then achieved by immobilizing said antibodies on the surface through Protein G, and blocking the non-binding sites by BSA, using spotting technique and fluorescent (fluorescein isothiocyanate, FITC)-labeled antibodies, as shown in FIG. 5. A drop of 0.2 mg/ml of protein G in HEPES buffer (50 mM, pH 7.4) was first placed on the surface ((a) in FIG. 5) and incubated for 10 min followed by a quick wash in a phosphate buffer (50 mM, pH 7.4). A bigger drop of 0.1 mg/ml of BSA in HEPES buffer (50 mM pH 7.4) was placed covering the area of the Protein G and a part of the bare GaAs surface ((b) in FIG. 5), and was incubated for 5 min. After washing with a phosphate buffer (50 mM, pH 7.4), a solution of FITC-labeled anti-human hemoglobin antibodies (0.1 mg/ml) in a phosphate buffer (50 mM, pH 7.4) was placed over the whole surface ((c,d) in FIG. 5), incubated for 10 min and washed in a phosphate buffer (50 mM, pH 7.4). Care has been taken that surface is not dried during the protein adsorption on the surface. As shown in FIG. 5, the area covered with BSA and anti-human hemoglobin antibodies only ((b) in FIG. 5) shows minimum fluorescence, indicating that BSA completely blocks the anti-human hemoglobin antibodies; the areas where bare GaAs or Protein G is present show a slightly higher fluorescence ((c,d) in FIG. 5); and the area covered with Protein G, BSA and anti-human hemoglobin antibodies ((a) in FIG. 5) shows the highest fluorescence, indicating that the antibodies are attached to the MPS-APS modified surface through Protein G, and that blocking of the non-binding sites by BSA is possible.

Figure 6:
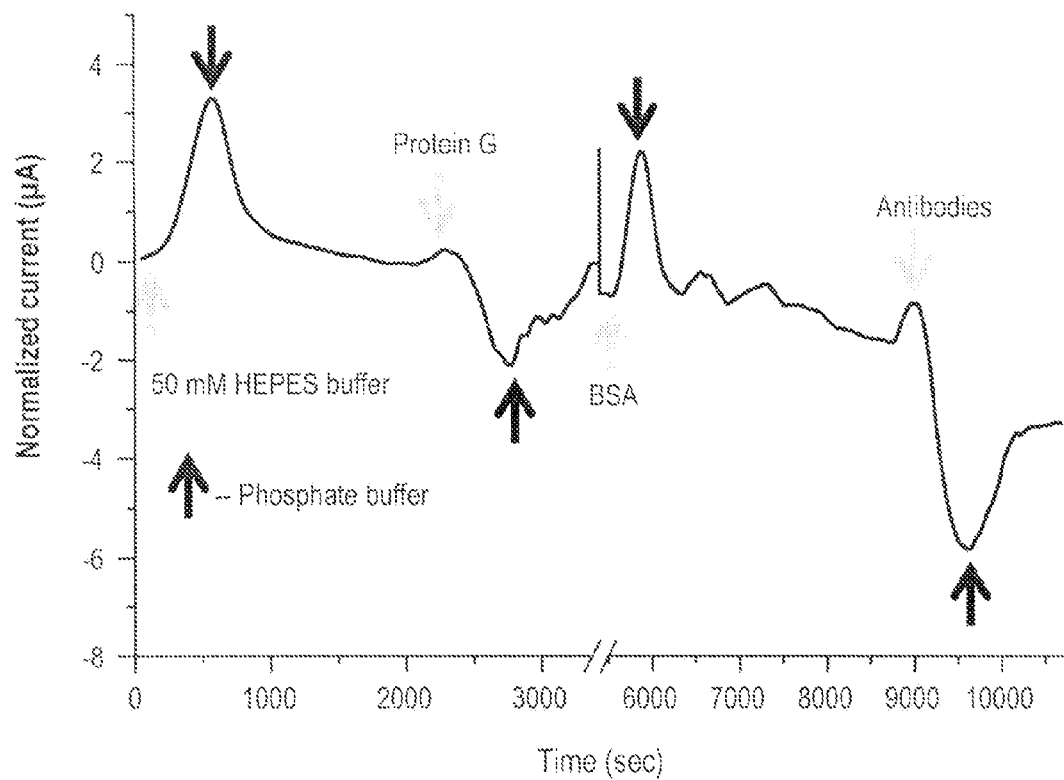
FIG. 6 shows normalized change in the MOCSER source-drain current as a function of time after sequentially adsorbing HEPES buffer (50 mM), Protein G (0.2 mg/ml), BSA (0.1 mg/ml), and anti-human hemoglobin antibodies (0.1 mg/ml), under 0.02 ml/min flow rate. The green arrows indicate the time when the device was exposed to the respective solutions as indicated in the graph, and the red arrows indicate the exposure of the device to phosphate buffer (50 mM) for washing.
Figure 7A:
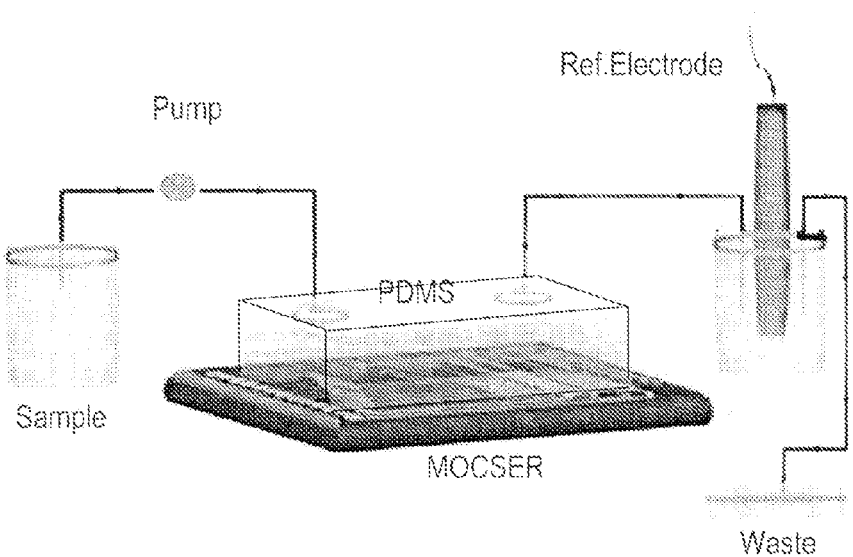
FIGS. 7A-7D show a schematic representation of the experimental setup used in the studies described in Example 1. (7A) A peristaltic pump was used to transfer analyte samples to a GaAs-based MOCSER on top of which a polydimethylsiloxane (PDMS)-based flow cell was constructed. An Ag/AgCl reference (Ref.) electrode was connected via a salt bridge. (7B) All electrical measurements were performed with wire bonded devices. The chip contained 16 devices from which 4 were selected and measured simultaneously. (7C) a schematic structure of the MPS and APS layers. (7D) The GaAs-based device (1; S: source; D: drain) was coated with 3-mercaptopropyltrimethoxysilane (MPS) layer and 3-aminopropyltrimethoxysilane (APS) (2), on top of which a lipid bilayer membrane was formed (3), and interactions with various analytes (4) were investigated.
Figure 7B:
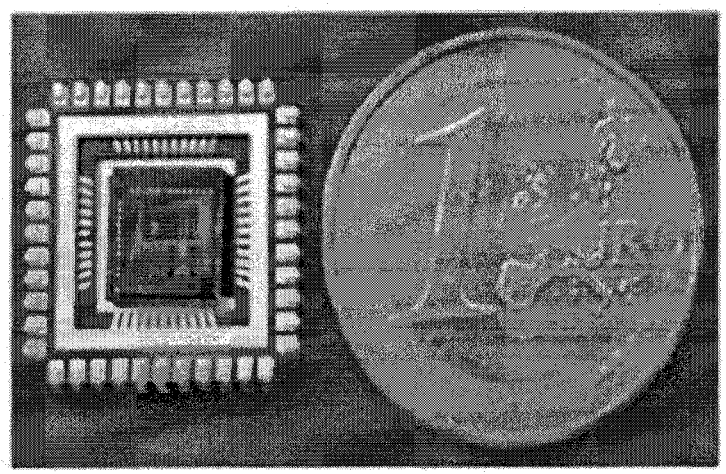
Figure 7C:
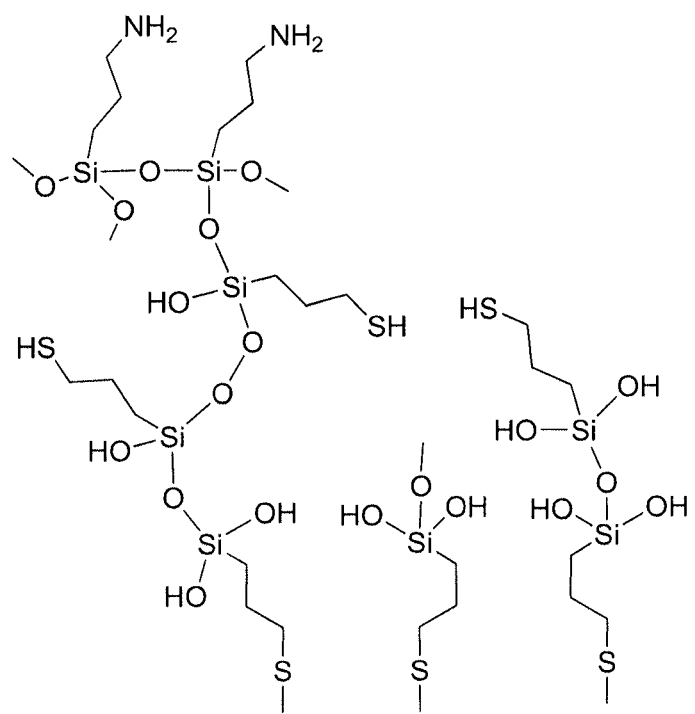
Figure 7D:
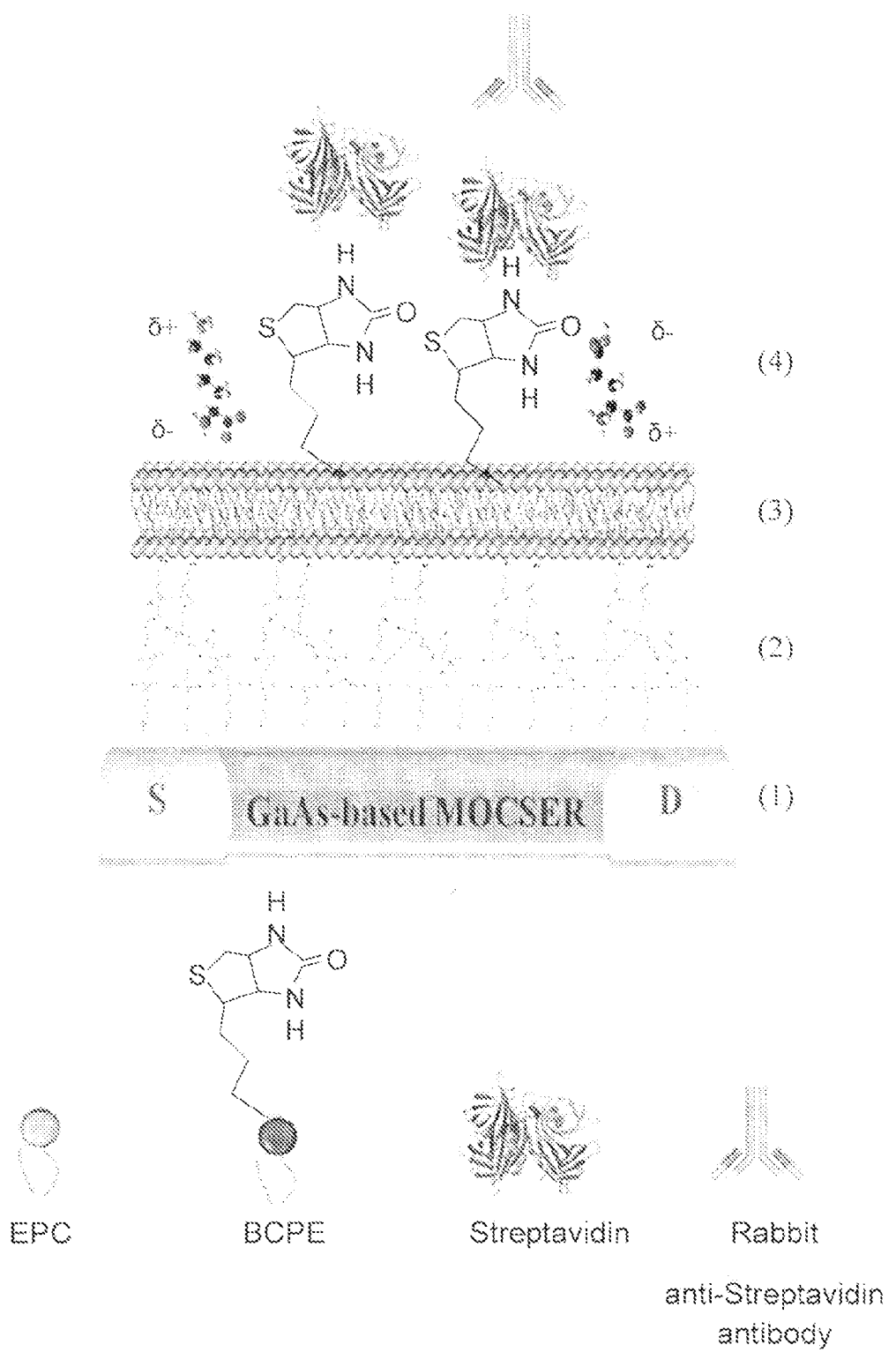

FIG. 6 shows the change in current of the MOCSER after sequentially adsorbing Protein G, BSA and anti-human hemoglobin antibodies. As shown, the net change in current is negative when Protein G is introduced into the sensing area; positive upon introducing of BSA; and negative during anti-human hemoglobin antibodies interaction with the surface of the device. According to the theory capacitive sensing in ISFETs (Ghafar-Zadeh et al., 2010), when a negative charge is accumulated on the surface of the device, it attracts positive charges in the gated area which in turn populates the conduction channel with more electrons leading to rise in current between source and drain, and vice versa. In contrast, although Protein G, BSA, anti-hemoglobin antibodies as well as hemoglobin are all negatively charged protein molecules at pH 7.4, in this experiment they showed a different behavior in terms of change in current, demonstrating that the sensing mechanism of the MOCSER is different from most generally accepted capacitive theory applicable for ISFETs.

Analytes and Solutions 3-mercaptopropyltrimethoxysilane (MPS; Cat. No. 63800) and 3-aminopropyltrimethoxysilane (APS; Cat. No. 15629TU) were purchased from Sigma. Egg phosphatidylcholin (EPC; Cat. No. 840051), 1,2-dioleoyl-sn-glycero-3- phosphoethanolamine-N-(lissamine rhodamine B sulfonyl) (LRBPE; Cat. No. 810150) and 1,2-dioleoyl-sn-glycero-3-phosphoethanolamine-N-(cap biotinyl) (BCPE; Cat. No. 870273) were obtained from Avanti polar lipids, Alabaster, Ala., USA. L-lysine, L-glutamic acid, avidin, streptavidin, rabbit anti-streptavidin antibody, mouse anti-streptavidin antibody and various phosphate buffer solutions with pH ranging from pH 6.0 to pH 8.0 were used in this study. L-lysine (Cat. No. L5501), L-glutamic acid (Cat. No. G1251), streptavidin (Cat. No. S4762), IgG rabbit anti-streptavidin antibody (Cat. No. S6390), human hemoglobin, *Streptococcus* Protein G, and bovine serum albumin (BSA) were obtained from Sigma. Mouse monoclonal anti-streptavidin antibody (Cat. No. ab10020) was purchased from Abcam. Sheep anti-human hemoglobin antibody (Cat. No. A80-135A) was purchased from Bethyl Laboratories. Sodium phosphate monobasic (Cat. No. 567545) and sodium phosphate dibasic (Cat. No. 567550) were obtained from Merck KGaA, Darmstadt, Germany. Deionized Milli-Q water was used for buffer preparation and experiments. Urine used has been collected once from a person in the laboratory.

Experimental Procedure for the Study Described in Example 1

Experimental setup is shown in FIG. 7. The surface of the device was modified with MPS-APS layers as described above, and the chip containing 16 MOCSERs was wire bonded for electrical measurements. All measurements were performed on 4 MOCSERs simultaneously, using Keithley 236 source-measure units and Keithley 2700 switch control, controlled and monitored by Labview application (version 8.2).

Polydimethylsiloxane (PDMS)-based flow cell (4 mm in length and width, and 0.6 mm in height) was fixed on top of the sensing area with epoxy glue. The PDMS prepolymer was made from a mixture of RTV 615 silicone compound and a curing agent (GE Silicones, Dandenong, Australia) at 10:1 ratio. Transferring of analyte and buffer solutions to the MOCSER devices was performed at 0.02 ml/min using a peristaltic pump (EP-1 Econo pump, Bio-Rad Laboratories, Israel) with teflon pipes (inner diameter of 0.8 mm).

Next, a lipid bilayer was formed on top of the device by introducing the lipids into the system with the peristaltic pump, as described above. After incubation, the sensing area was rinsed with a phosphate buffer. In order to preserve the membrane, the MOCSER devices were kept in liquid medium during the measurement. The analytes were dissolved in the phosphate buffer and were injected sequentially into the flow cell. Different concentrations were obtained by mixing the analytes with phosphate buffer solution (concentrations, volumes and flow-rates are provided in Table 1). Phosphate buffer solution was injected sequentially between analytes, using teflon pipes with an inner diameter of 0.8 mm, to rinse the sensing area and remove analyte excess. The signal measured during this time was used as a baseline in the data analysis. Phosphate buffer (0.05 M, pH 7.0) was used in all experiments except in the case of monoclonal mouse anti-streptavidin antibody, where phosphate buffer (0.05 M, pH 7.4) was used.

A constant potential of 1.0 V was applied between source and drain of the MOCSER devices, and the change in the source-drain current were monitored as a function of time for all four selected channels simultaneously. An Ag/AgCl pseudo reference electrode was placed in a sealed tube and connected via a salt bridge to maintain a stable and constant potential over the surface of the MOCSER devices.

TABLE 1

Analytes used in the study described in Example 1

| Analyte | Concentration* | Sample volume | Flow rate | Membrane |
|---|---|---|---|---|
| L-lysine | 1.6-50 µmole | 250 µl | 0.02 ml/min | 1) EPC<br>2) no membrane |
| L-glutamic acid | 0.4-50 µmole | 250 µl | 0.02 ml/min | 1) EPC<br>2) no membrane |
| Phosphate buffer solutions with pH ranging from 6.0 to 8.0 | 0.05M | 500 µl | 0.02 ml/min | 1) EPC<br>2) no membrane |
| Streptavidin/ Avidin | 0.07-80 nmole | 100 µl | 0.01 ml/min | 1) EPC-BCPE (8:2)<br>2) EPC |
| 1) Rabbit anti-streptavidin antbody | 0.15-1 mg/ml | 250 µl | 0.01 ml/min | 1) EPC-BCPE (8:2)-streptavidine<br>2) EPC |
| 2) Mouse anti-streptavidin antbody | 0.15-1 mg/ml | | | |
| 3) Rabbit serum | — | | | |

*Since a phosphate buffer solution (0.05M, pH 7.0) was injected sequentially between different analytes to remove analyte excess, analytes were diluted with the phosphate buffer. Therefore, amounts of analyte molecules and volume are indicated separately.

Experimental Procedure for the Study Described in Example 2

Figure 8:
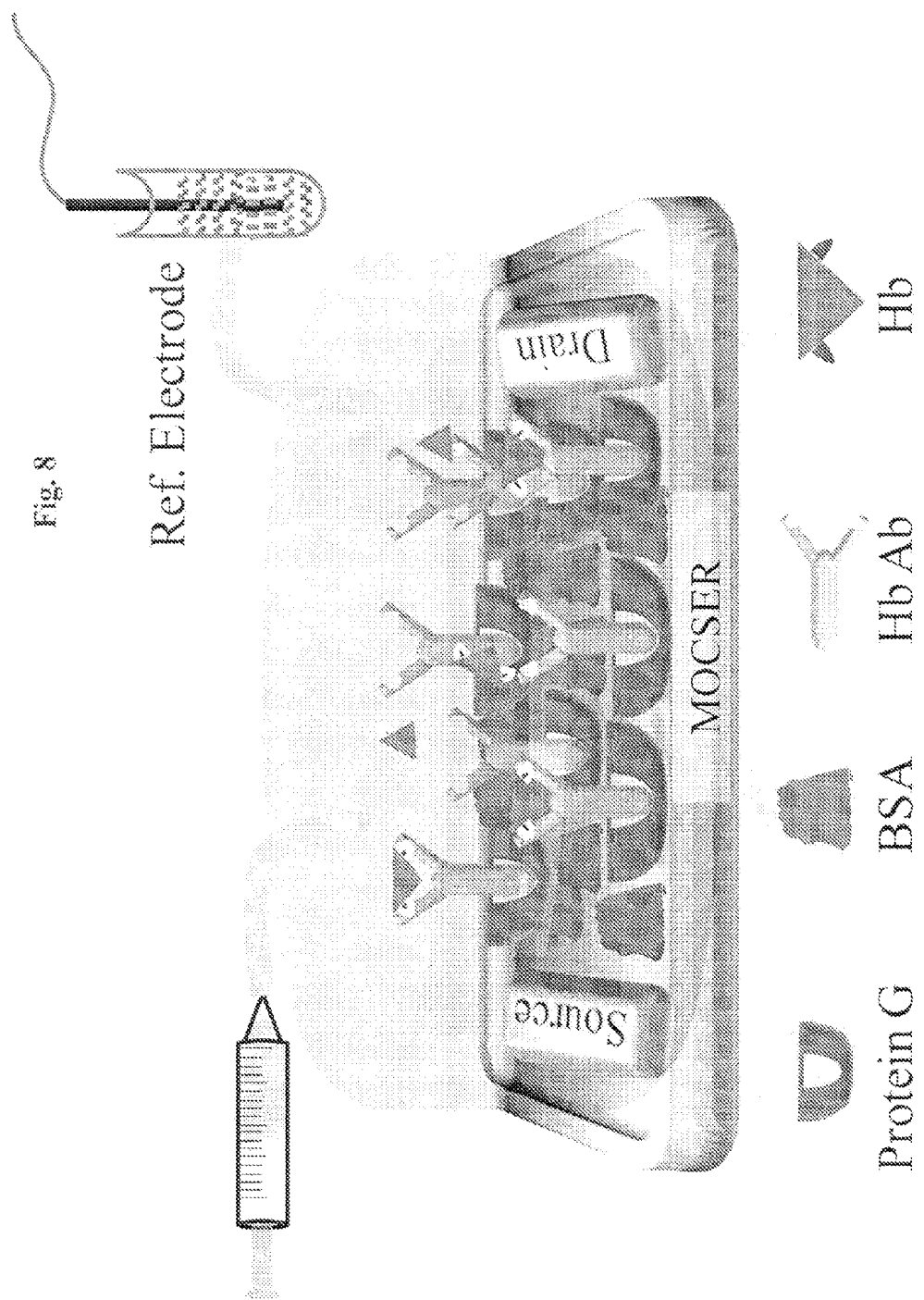
FIG. 8 shows a schematic representation of the experimental setup used in the studies described in Example 2. Syringe pump was used to transfer analyte samples to a GaAs-based MOCSER on top of which a PDMS-based microfluidic flow cell was constructed. An Ag/AgCl reference (Ref.) electrode was connected via a salt bridge. Sheep anti-human hemoglobin antibodies (Hb Ab) were attached to the MPS-APS modified GaAs surface through Protein G, followed by BSA blocking of the non-binding sites. Hb—human hemoglobin.

Experimental setup is shown in FIG. 8. The surface of the device was modified with MPS-APS layers as described above, and the chip containing 16 MOCSER devices was wire bonded for electrical measurements. All measurements were performed on 4 MOCSERs simultaneously, using Keithley 236 source-measure units and Keithley 2700 switch control, controlled and monitored by Labview application (version 8.2).

PDMS-based flow cell (4 mm in length and width, and 0.6 mm in height) was fixed on top of the sensing area with epoxy glue. The PDMS prepolymer was made from a mixture of RTV 615 silicone compound and a curing agent (GE Silicones, Dandenong, Australia) at 10:1 ratio. Transferring of analyte, buffer solutions and urine solutions to the MOCSER devices was performed at 0.02 ml/min using a syringe pump (Harvard Apparatus, PHD Ultra). Sensing of hemoglobin was performed through the binding of hemoglobin in the analyte introduced to its antibodies.

A constant potential of 1.0 V was applied between source and drain of the MOCSER devices, and changes in source-drain current were monitored as a function of time for all four selected channels simultaneously. An Ag/AgCl pseudo reference electrode was placed in a sealed tube and connected via a salt bridge to maintain a stable and constant potential over the surface of the MOCSER devices.

Example 1

The Response of the Membrane-Coated GaAs-Based MOCSER to Various Analytes

Figure 9A:
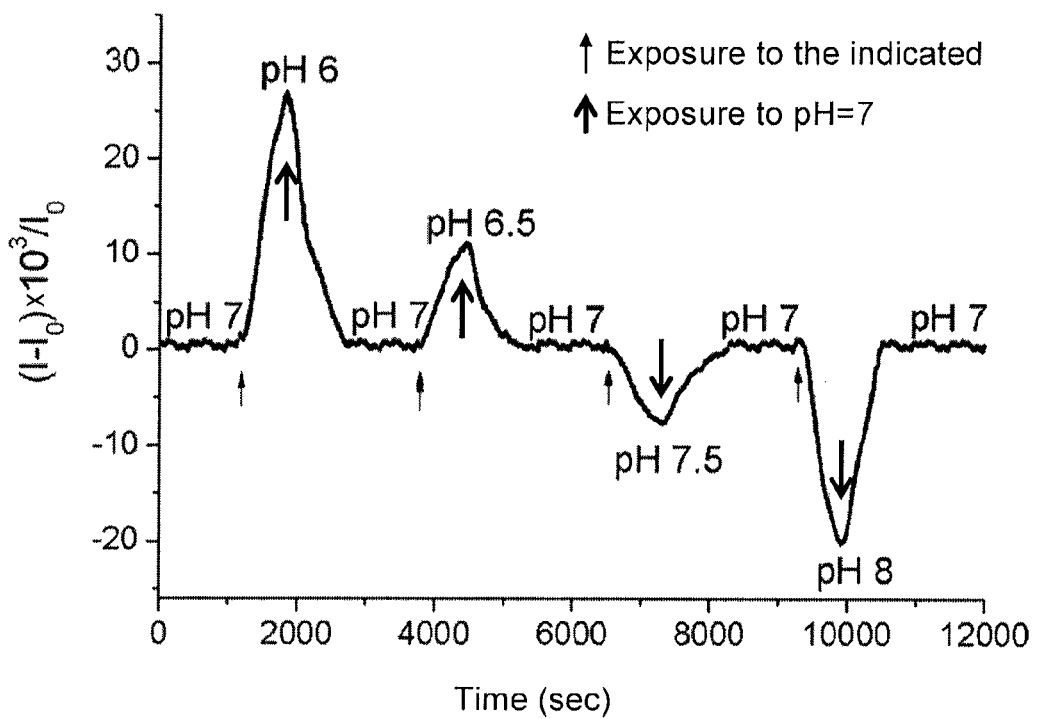
FIGS. 9A-9B show normalized change in the MOCSER source-drain current as a function of time when sequentially exposing the EPC-based membrane adsorbed on the device to a phosphate buffer solution (0.05 M) at a pH ranging between pH 6.0 to 8.0 under a laminar flow of 0.02 ml/min (9A); and normalized response curve based on the derivative (slope) of the change in the signal in the peaks' half-maximum for different pH solutions (9B).
Figure 9B:
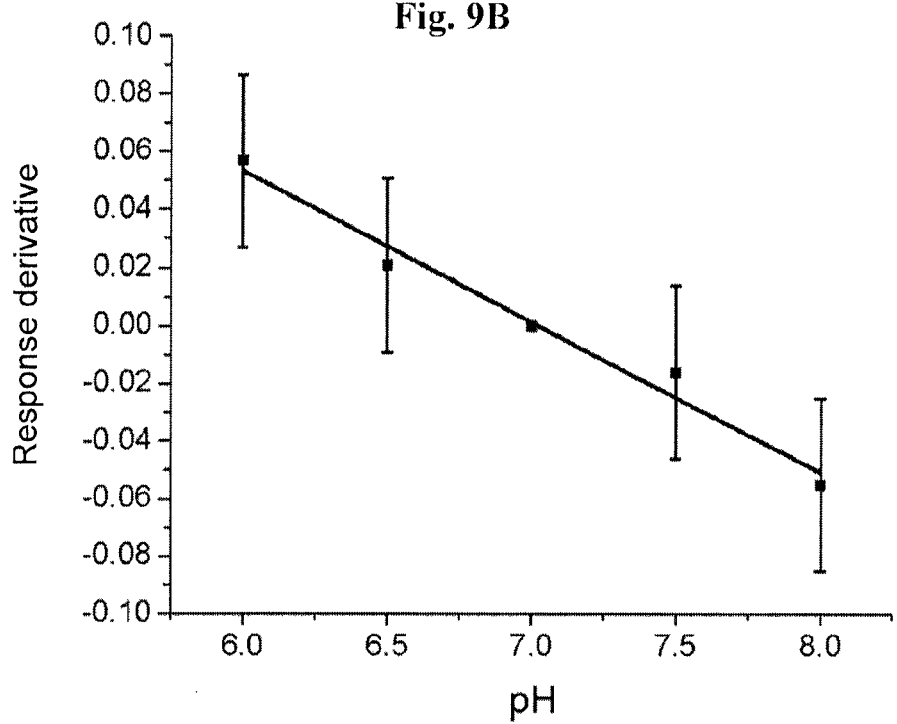

FIG. 9 shows the change in the current through the MOCSER when the device is exposed to phosphate buffer solutions with pH ranging from 6.0 to 8.0. As shown, following the time it takes the solution to reach the sensor, the MOCSER source-drain current response to pH change is immediate and stable (FIG. 9A), and the response of the device to pH is linear within the range studied (FIG. 9B).

Figure 10A:
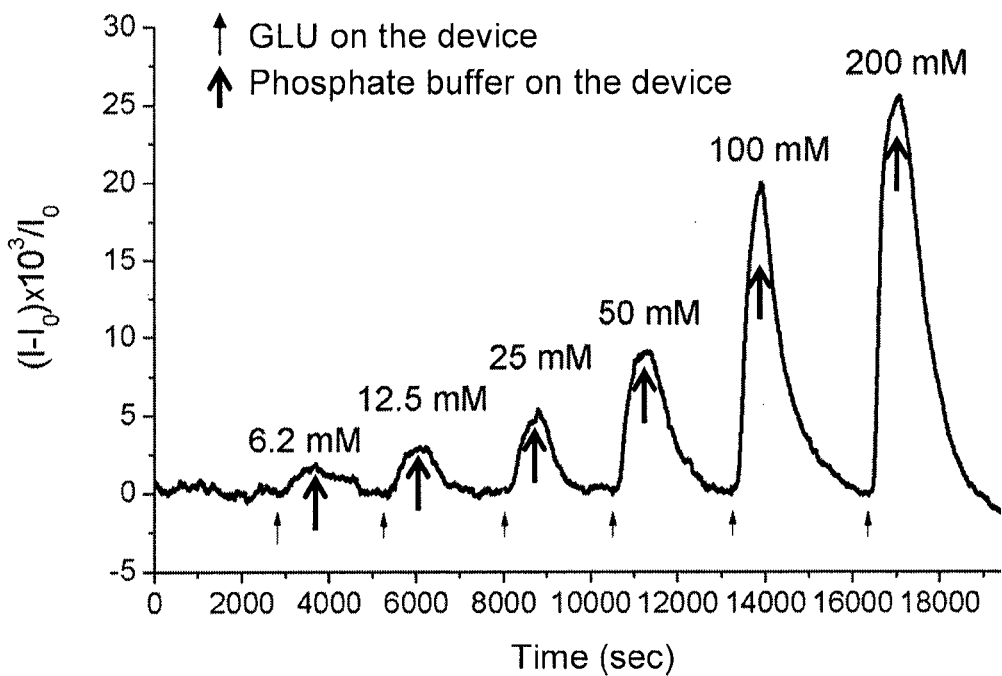
FIGS. 10A-10B show (i) normalized change in the MOCSER source-drain current as a function of time when membrane-coated GaAs devices were exposed to various concentrations of L-glutamic acid (GLU). A rapid increase in the current was observed upon injection of GLU, and the current decreased when the GLU was washed out by phosphate buffer (10A); and (ii) a plot of the change in the normalized current (the derivative of the signal) using either MPS-APS-modified GaAs devices or devices additionally covered by an EPC-membrane (10B).
Figure 10B:
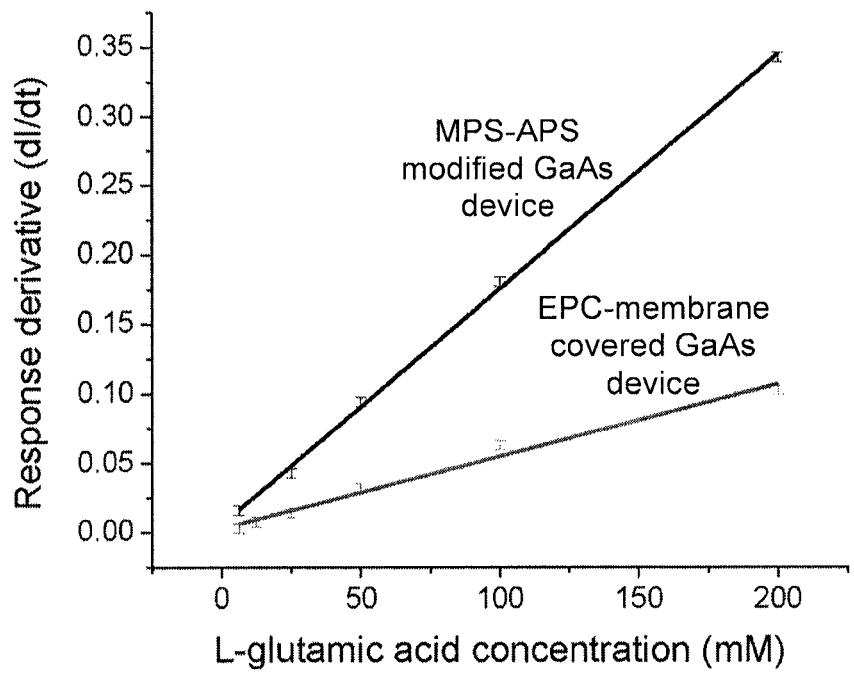
Figure 11A:
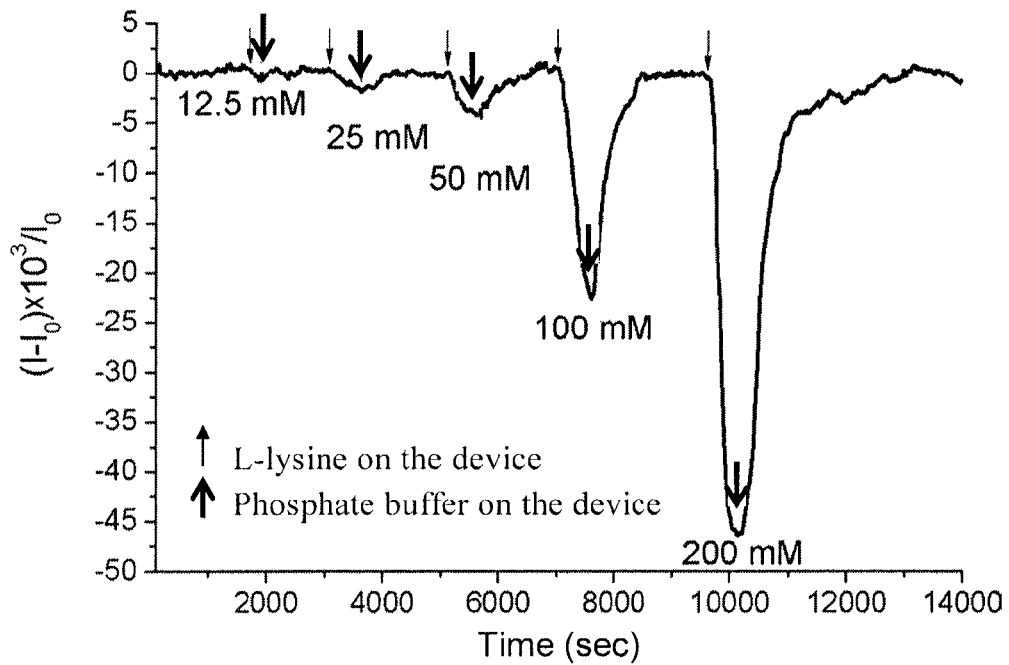
FIGS. 11A-11B show (i) normalized change in the MOCSER source-drain current as a function of time when membrane-coated GaAs devices were exposed to various concentrations of L-lysine. A rapid decrease in the current was observed in the presence of L-lysine, and the current increased when the L-lysine was washed out by phosphate buffer (11A); and (ii) a plot of the change in the normalized current (the derivative of the signal) in the case of MPS-APS-modified GaAs devices and the devices additionally covered by EPC-membrane.
Figure 11B:
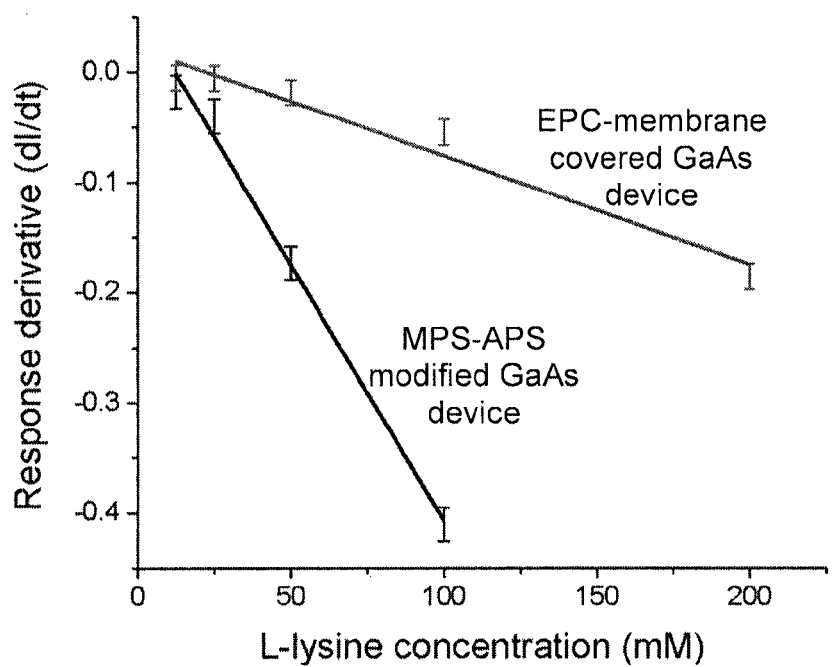

Changes in the source-drain current of the membrane-coated MOCSER device were observed when it was exposed to various concentrations of negatively- or positively-charged amino acids at pH=7, exemplified by L-glutamic acid (FIG. 10) or L-lysine (FIG. 11), respectively. As shown, the MOCSER source-drain current response is correlated with the concentration of the analyte molecules. While the current increased as the concentration of L-glutamic acid increased, it decreased with increasing L-lysine concentration. The calibration plots are obtained by plotting the derivative of the signal as a function of time vs. the analyte concentration (FIGS. 10B and 11B). The change in the signal upon exposure of the sensor to the analyte depends on the flow rate in the microfluidic device; the specific response of the MOCSER to the analyte; and the analyte concentration. Since the flow rate was maintained constant through all the measurements and the only parameter varying was the analyte concentration, the derivative gradient of the signal should be proportional to the analyte concentration. Indeed, the signal derivative as measured at about 200 sec after exposure to the analyte solution was found to be proportional to the concentration of the analyte. Monitoring the gradient instead of the maximum current ensures better reproducibility of the signal and eliminates contribution from baseline shift.

The detection thresholds for L-lysine and L-glutamic acid in the presence of EPC membrane were about 12.5 mM and 6.2 mM, respectively, and they improved to 3.2 mM and 1.6 mM for L-lysine and L-glutamic acid, respectively, in the absence of the membrane. These data further confirm the existence of the membrane on the MOCSER. Clearly, the membrane reduces the sensitivity of the device by about a factor of four.

It is interesting to note that while the change in the signal, in the case of the pH measurements, is proportional to the logarithmic change in the concentration of the protons, it was almost linearly dependent on the concentration of the amino acids. This phenomenon is not related to the existence of the membrane and hence indicates that there is a different mechanism for the effect of both type of species (protons and organic acids) on the MOCSER.

Figure 12:
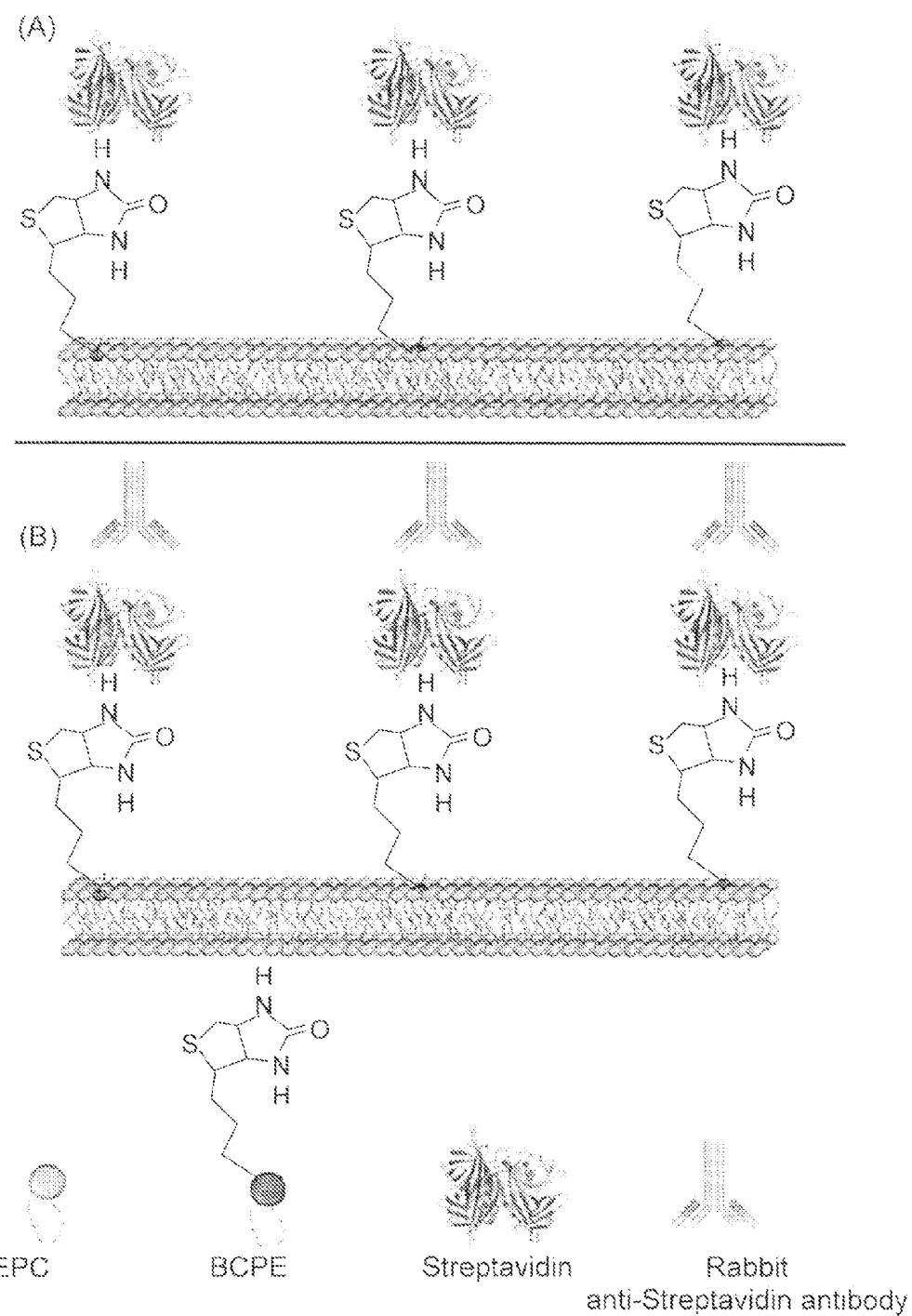
FIG. 12 shows schematic illustration of the strategy used for surface modification with streptavidin (panel A) and rabbit anti-streptavidin antibody (panel B) for detection by the devices coated with a biotinylated membrane (EPC-BCPE (8:2)).
Figure 13A:
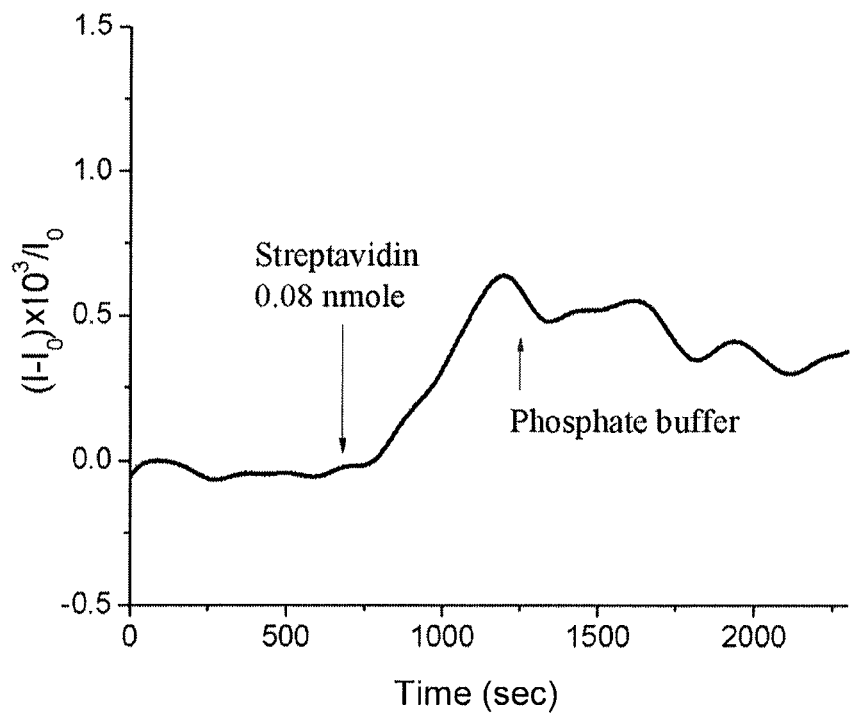
FIGS. 13A-13B show the response of a MOCSER device coated with biotin-containing EPC-BCPE (8:2) membrane upon exposure to streptavidin (13A) and avidin (13B) molecules. In both cases, the indicated amount of material was dissolved in 100 μl.
Figure 13B:
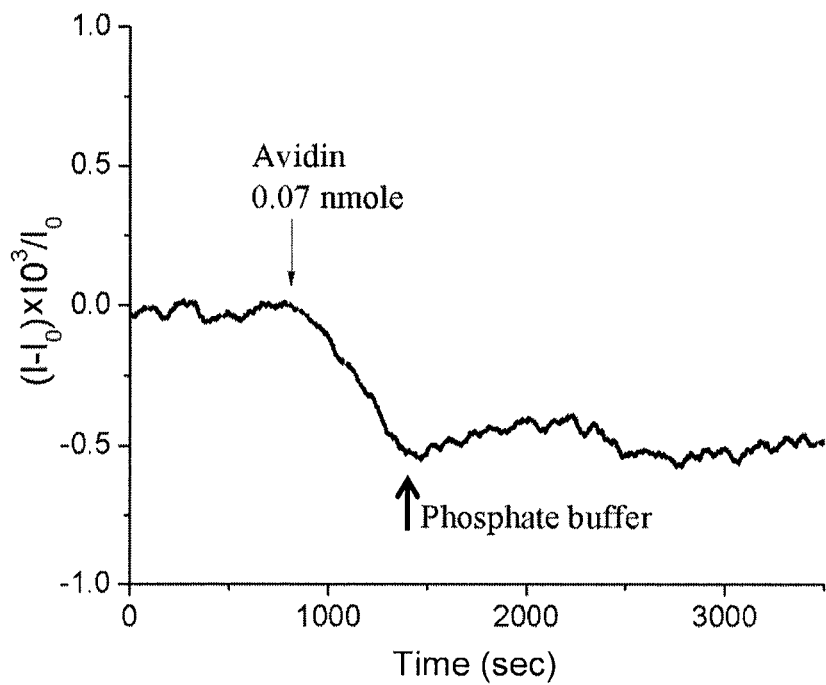

For streptavidin and rabbit anti-streptavidin antibodies detection, the strategy presented in FIG. 12 was used, utilizing an EPC-BCPE (8:2) membrane containing a fraction of ~20% biotin. Attachment of streptavidin to the membrane was evidenced and characterized by AFM using 50 nm EPC-BCPE (498:1) vesicles as a marker. The 50 nm EPC-BCPE (498:1) vesicles were not observed in the absence of streptavidin. Exposing the membrane to either streptavidin or avidin at concentrations above 0.8 µM at pH=7 resulted in a significant change in the MOCSER source-drain current. The current increased upon exposure to streptavidin concentration increase (FIG. 13A), but the signal did not recover when the solution was changed to buffer with no streptavidin, indicating a strong (and seemingly irreversible on the time scale of the experiment) binding of the streptavidin to the biotin. When exposed to avidin, the current through the MOCSER was reduced (FIG. 13B). When a membrane without biotin (EPC-based membrane) was exposed to the same solution, a change in the current was observed; however, this change could be completely reversed by washing with buffer.

While streptavidin is negatively charged at neutral pH, avidin is positively charged. Hence a reverse effect on the current is observed in accordance with the observations when amino acids were probed, generally indicating that a negatively charged analyte causes an increase in the current through the MOCSER while a positively charged analyte causes a decrease in the current.

Figure 14A:
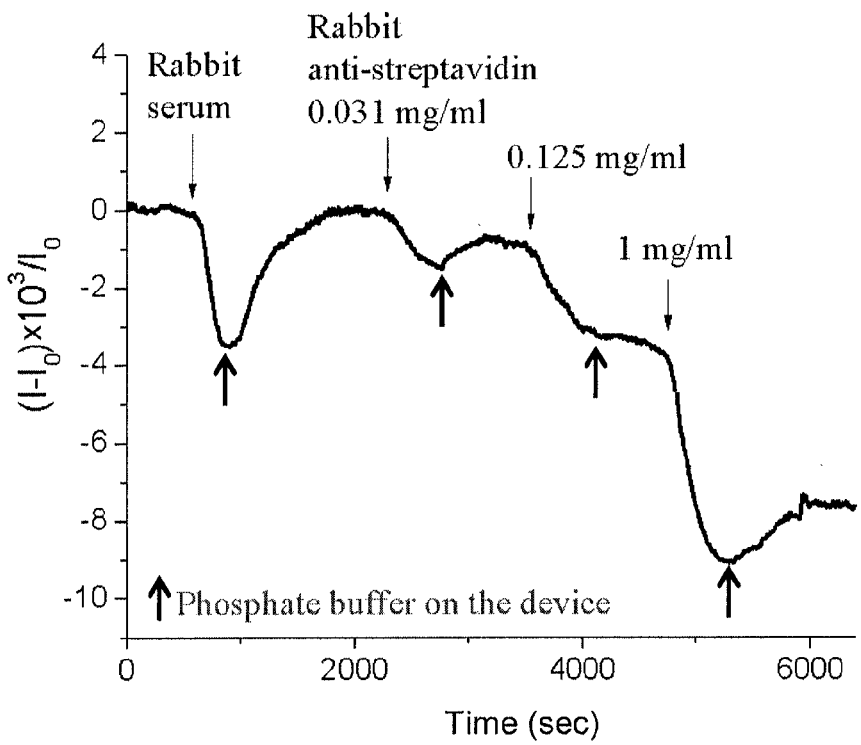
FIGS. 14A-14D show (i) normalized change in the MOCSER source-drain current as a function of time when exposed to different concentrations of rabbit anti-streptavidin antibody (whole antiserum) and rabbit serum alone (no antibodies). After exposure to serum, the signal recovered to the baseline when washed with a phosphate buffer, while there was a non-reversible baseline offset in case of exposure to the anti-streptavidin antibody solution, resulting from specific interaction between immobilized streptavidin and rabbit anti-streptavidin antibodies (14A); (ii) normalized change in current when the device was exposed to different concentrations of mouse anti-streptavidin antibody (purified). In this case, the signal exhibited non-reversible baseline offset upon washing with the buffer solution (14B); (iii) calibration curve for response due to strong interaction of rabbit anti-streptavidin antibody with streptavidin, compared with the weak interaction of the same antibodies with non-biotinylated membrane (14C); and (iv) calibration curve for response due to interaction of mouse anti-streptavidin antibody with streptavidin (14D).

Change in the MOCSER source-drain current was observed when devices to which streptavidin were initially attached were exposed to polyclonal rabbit anti-streptavidin antibody in serum (FIG. 14A, right). In this case, the current decreased upon exposure to the antibodies at concentrations of 0.031, 0.125 and 1 mg/ml. Irreversible negative offset in the current was observed following washing with a buffer solution indicating binding of the anti-streptavidin molecules to the biotin-streptavidin complex. However, when the serum contained no antibodies, the signal returned to the baseline upon washing (FIG. 14A, left). The fact that the signal is not returning to the baseline when the antibodies are present reflects the strong binding of the antibody to the streptavidin. As a control experiment, devices with no biotin (EPC-based membrane) and hence no bound streptavidin were exposed to the same antibody containing-serum solution. A small positive offset in the current was observed upon washing, indicating non-specific binding of serum species to the membrane. The normalized response of the current is plotted in FIG. 14C as a function of the amount of antibodies to which they were exposed. The amount of analyte (and not its concentration) is presented since the binding of the analyte is seemingly irreversible and the signal is accumulating as a function of the amount of analyte to which the sensor is exposed. The two curves relate to devices coated with biotinylated membrane (EPC-BCPE (8:2) based membrane) to which streptavidin was attached and to devices coated with a membrane (EPC-based membrane) without biotin.

Figure 14B:
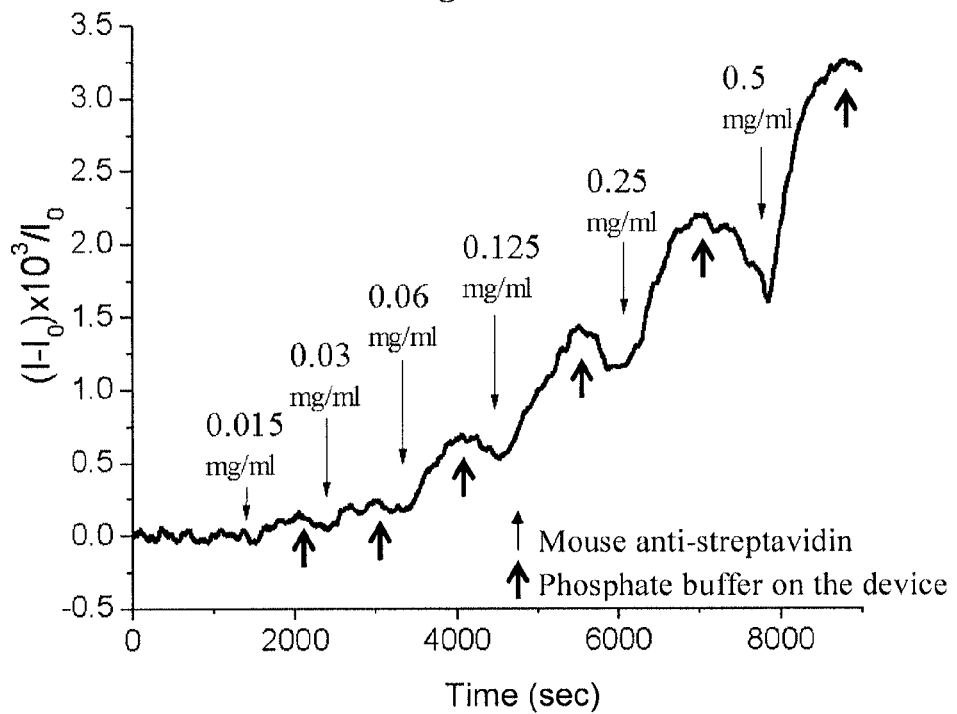
Figure 14C:
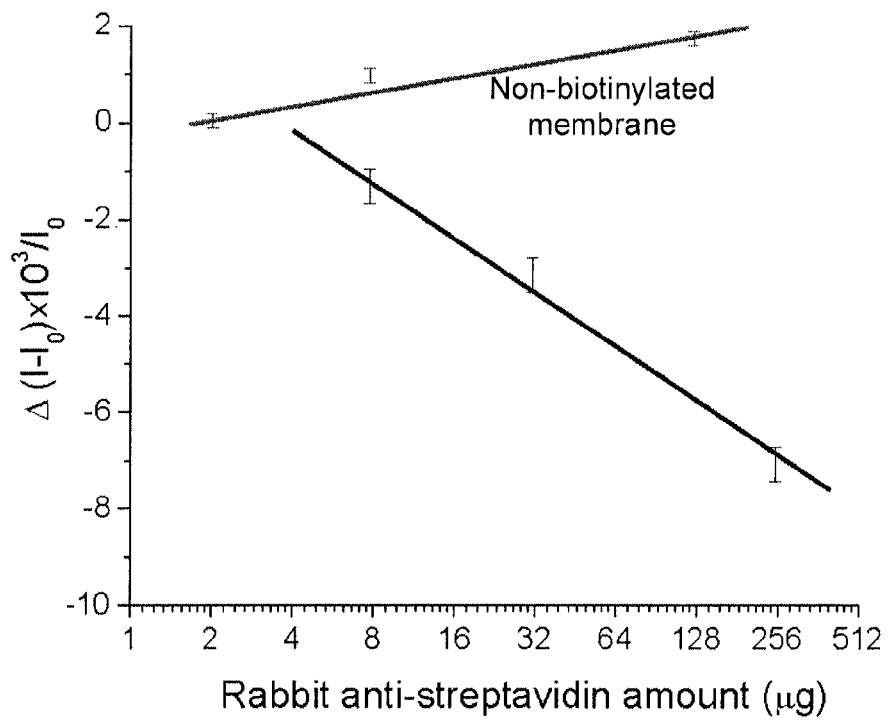
Figure 14D:
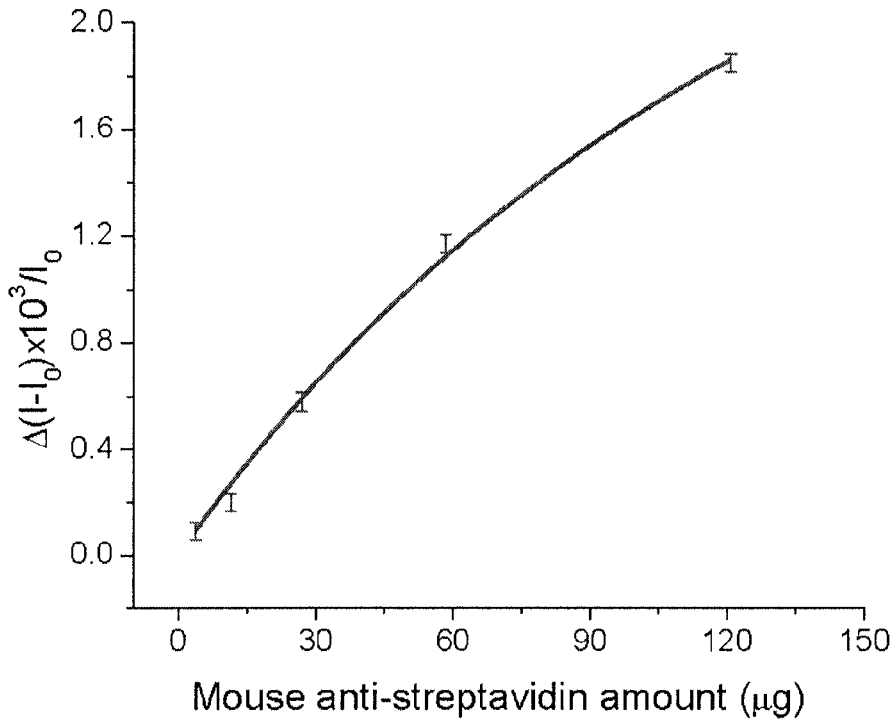

For comparison, FIG. 14B shows the normalized change in the current obtained when the device was exposed to various concentrations of monoclonal mouse anti-streptavidin antibody. In this case, the signal increased upon exposure to the antibodies and exhibited a baseline offset upon washing with the buffer solution. The difference in the trend of the response (negative vs. positive offset in FIGS. 14A and 14B, respectively) is probably due to different charge on each type of antibody. The normalized response of the current through the MOCSER due to interaction of mouse anti-streptavidin antibody with streptavidin is shown in FIG. 14D. Here, clearly a nonlinear response of the device to the concentration is observed. The non-linearity in the response is not evident in other cases (FIG. 14C) because of the limited range of the analyte concentration to which the sensor was exposed and due to the low number of data points that do not allow a nonlinear fit.

Figure 15:
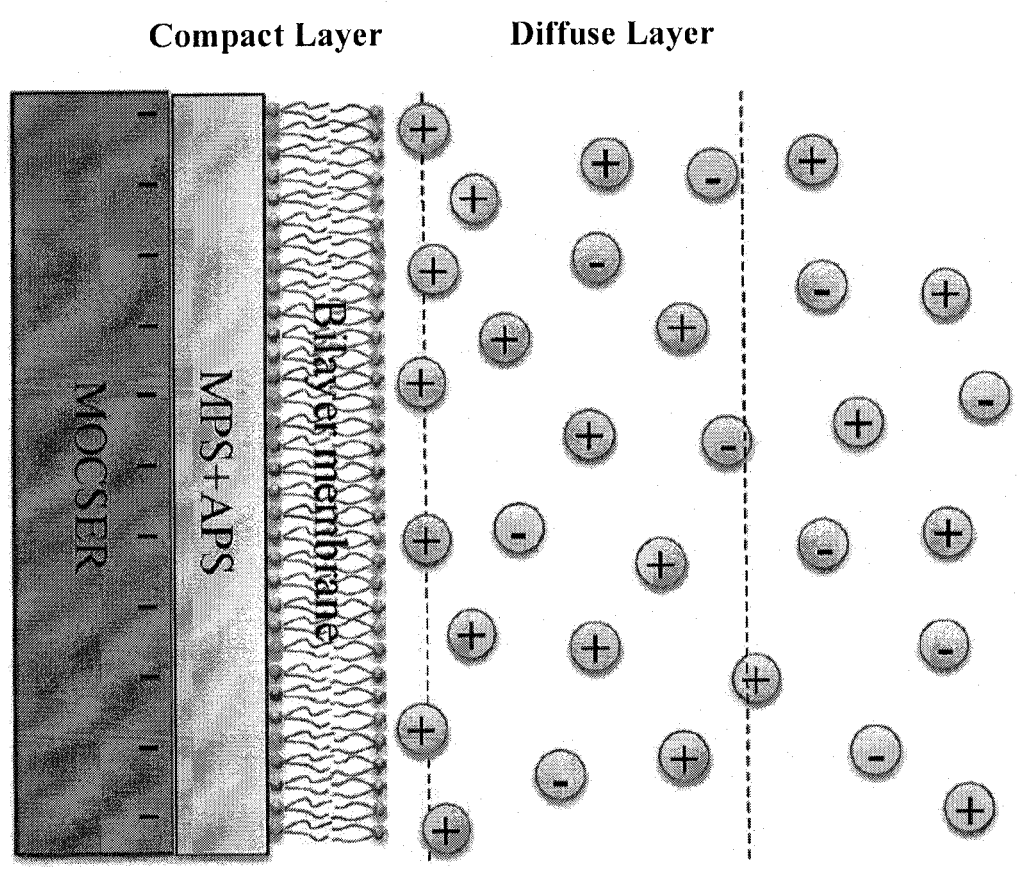
FIG. 15 shows a scheme of the double layer formed on the surface of the MOCSER. The MPS layer is not in scale, and in reality, it is about a hundred times thicker than the bilayer membrane. In the case of high concentration of cations in the double layer, the MOCSER surface is negatively charged and the current through the MOCSER decreases, while for high anion concentration, the MOCSER surface becomes positively charged and the current through the MOCSER increases.

The results presented above indicate that the operation of the MOCSER as a sensor is based on the fact that it is capacitance sensitive. Thus, when the device is immersed in electrolyte solution with a reference electrode, a double layer is formed on its surface, as shown in FIG. 15. Clearly, when the analyte on the surface of the membrane is negatively charged, the charge accumulating on the surface of the device is positive and vice versa. Since the device is based on n-doped GaAs, positive charge on the surface increases the charge carrier concentration in the conductive channel and the source-drain current increases. The opposite is true for negative charge on the surface of the GaAs that causes depletion in the charge carrier concentration and hence reduction in the source-drain current.

Example 2

Figure 16:
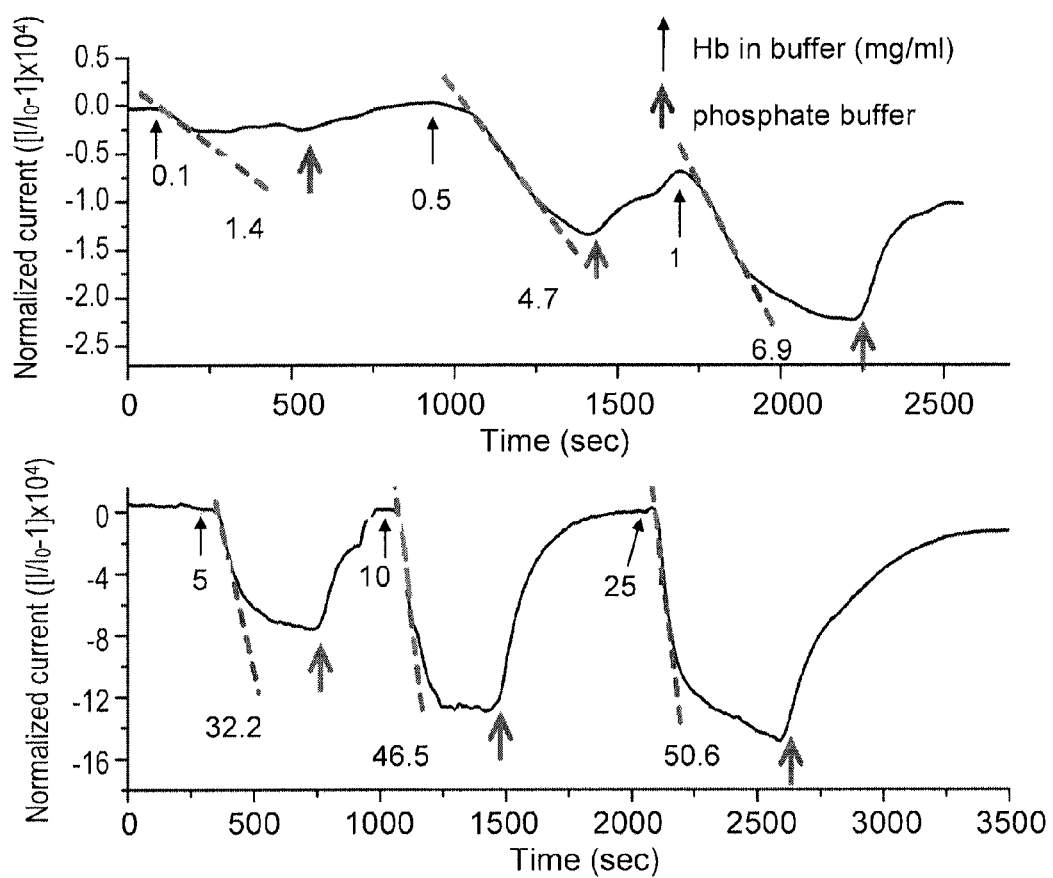
FIG. 16 shows normalized change in the MOCSER source-drain current as a function of time when sequentially exposed to hemoglobin (Hb) dissolved in phosphate buffer (50 mM), at the concentrations indicated in the graph under 0.02 ml/min flow rate. The gradient of response (normalized response) is shown in bold.
Figure 17:
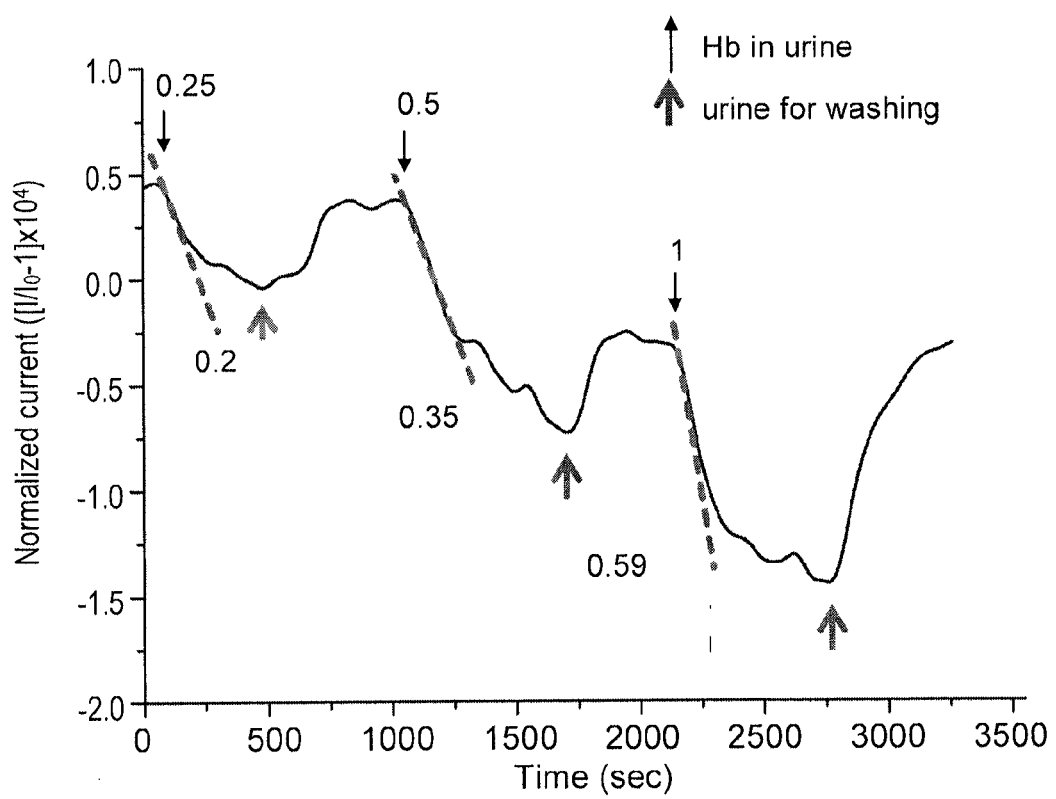
FIG. 17 shows normalized change in the MOCSER source-drain current as a function of time when sequentially exposed to hemoglobin (Hb) dissolved in urine, at the concentrations indicated in the graph under 0.02 ml/min flow rate. The gradient of the response (normalized response) is shown in bold.
Figure 18:
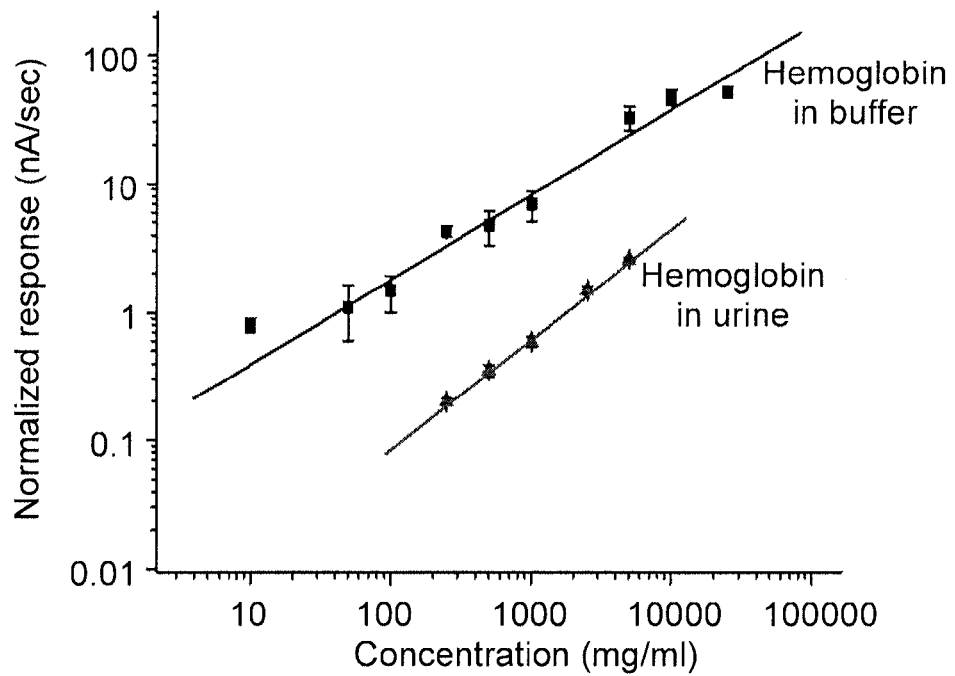
FIG. 18 shows a calibration plot representing the normalized change in the current measured in the MOCSER upon exposure to different concentrations of hemoglobin in phosphate buffer (50 mM) and in urine, based on the gradient of the change in the source-drain current as a function of time.

The Membrane-Coated GaAs-Based MOCSER is Capable of Detecting the Presence of Hemoglobin in Urine In this study, phosphate buffer (50 mM, pH 7.4) was first used as a model system, i.e., as a carrier buffer for the hemoglobin, and was injected sequentially between analytes to rinse the sensing area and remove analyte excess. Then, hemoglobin was dissolved in urine, and urine was injected between analytes to rinse the sensing area. FIG. 16 shows the change in the source-drain current through the MOCSER when the device was exposed to phosphate buffer-based hemoglobin solutions with concentrations of 0.1, 0.5, 1, 5, 10 and 25 mg/ml, and FIG. 17 shows the change in the source-drain current through the MOCSER when the device was exposed to urine-based hemoglobin solutions with concentrations of 0.25, 0.5 and 1 mg/ml. As shown in FIGS. 16 and 17, the device response is immediate and stable upon exposure to the hemoglobin solutions. The current measured in the MOCSER decreases when hemoglobin interacts with the anti-hemoglobin antibodies attached to the MPS-APS-modified surface, and recovers after washing hemoglobin with the phosphate buffer or urine, wherein the signal is correlated with the concentration of the analyte molecules. A calibration plot, obtained by plotting the slope of the signal as a function of time vs. the analyte concentration, is shown in FIG. 18.

Since all other parameters during the measurement were kept constant and only the concentration of analyte was changed, the slope of the signal should be proportional to the concentration of the analyte. Monitoring the gradient instead of the net change in the current ensures better reproducibility of the signal and eliminates contribution from baseline shifts. As found, the sensitivity of the MOCSER to hemoglobin, based on these experiments, was 10 µg/ml and 100 µg/ml of hemoglobin in phosphate buffer and urine, respectively, representing the lower detection limit for the current setup. The sensitivity of the MOCSER to hemoglobin in urine was lower than in phosphate buffer, probably due to the fact that the urine salt concentration is much higher.

Figure 19:
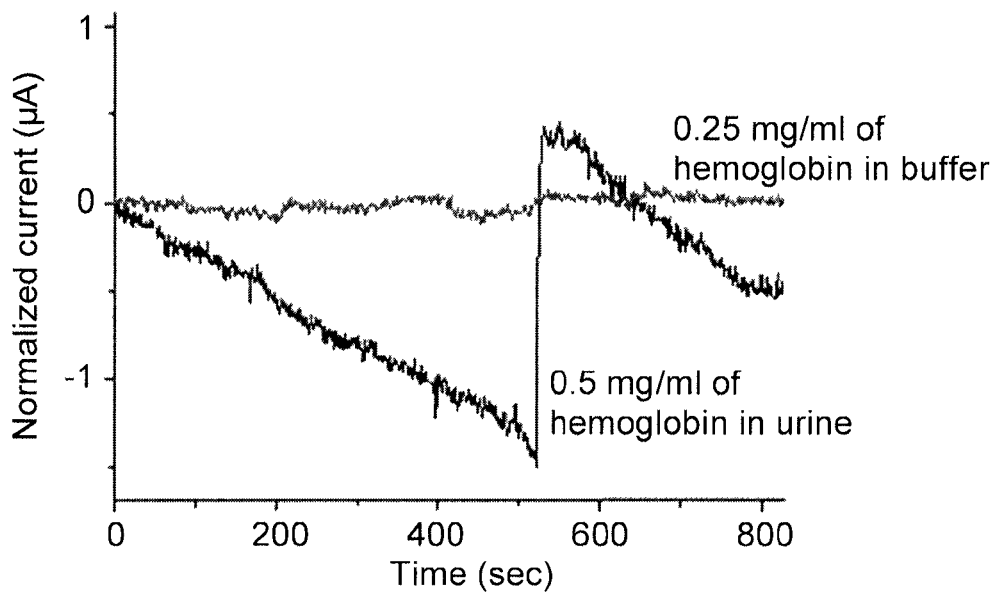
FIG. 19 shows normalized change in the MOCSER source-drain current as a function of time when sequentially exposed to human hemoglobin (Hemo; 0.5 mg/ml or 0/25 mg/ml) dissolved in urine and phosphate buffer, respectively, without sheep anti-human hemoglobin antibodies attached to the MPS-APS modified surface. Hemoglobin was introduced as indicated and there was no response of the MOCSER when anti-hemoglobin antibodies were not present.
Figure 20:
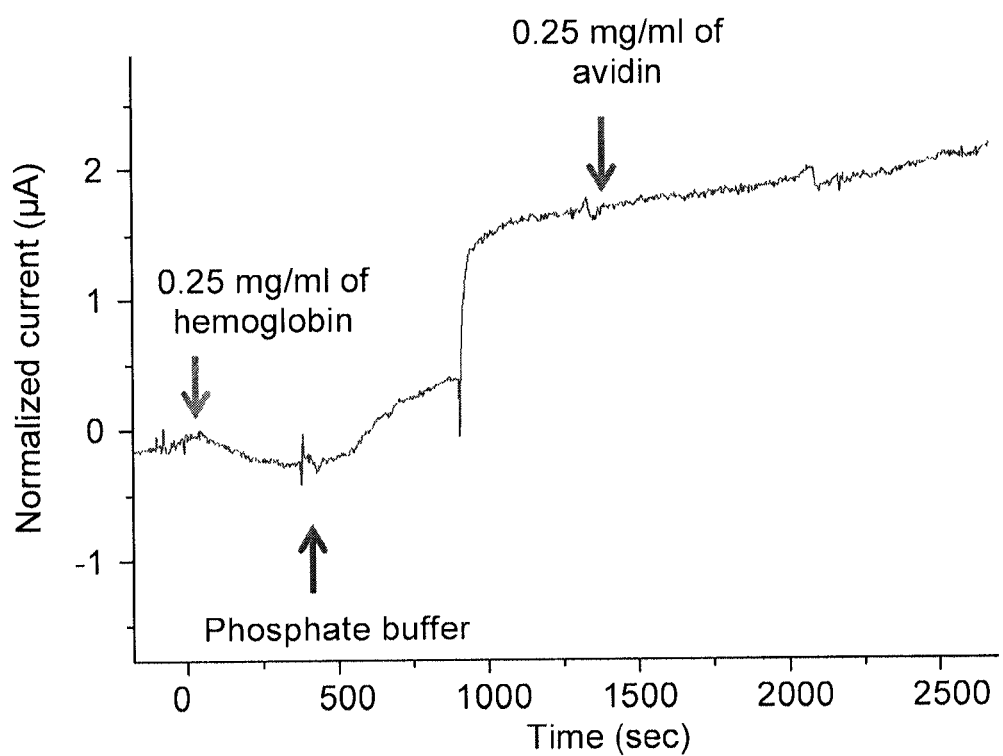
FIG. 20 shows normalized change in the MOCSER source-drain current as a function of time when sequentially exposed to hemoglobin (Hemo) and avidin as indicated. While in response to hemoglobin, the MOCSER responded as shown, no response was shown after exposure to avidin, indicating the specificity of the device.

The high selectivity of the MOCSER results from the antibody-antigen interaction. Thus, in order to verify the selectivity of the MOCSER, the source-drain current in response to hemoglobin solutions in phosphate buffer, when sheep anti-human hemoglobin antibodies are not immobilized on the gate area, and the surface is only functionalized with protein G and BSA, was measured. As found and shown in FIG. 19, no response to the hemoglobin analytes was observed, indicating the high selectivity of the MOCSER, and these results were consistent when current was measured in response to urine-based hemoglobin solutions. Nevertheless, when a very high concentration of hemoglobin was used, a non-specific response was observed, but that response was completely random and could not be correlated with the hemoglobin concentration. In order to verify the specificity of the MOCSER, analytes containing avidin, representing a non-specific antigen, were introduced to a MOCSER having a gate area on which sheep anti-human hemoglobin antibodies were immobilized, and as shown in FIG. 20, no change in the current was observed, demonstrating the high specificity of the device.

REFERENCES

Baciu, C. L., Becker, J., Janshoff, A., Sönnichsen, C., *Nano Letters,* 2008, 8, 1724-1728

Barenholz, Y., Gibbes, D., Litman, B. J., Goll, J., Thompson, T. E., Carlson, R D., *Biochemistry,* 1977, 16, 2806-2810

Baumann, W. H., Lehmann, M., Schwinde, A., Ehret, R., Brischwein, M., Wolf, B., *Sens. Actuators, B* 1999, 55, 77-89

Bergveld, P., *IEEE Trans Biomed Eng.,* 1972, 19, 342-351

Bergveld, P., DeRooij, N. F., Zemel, J. N., *Nature,* 1978, 273, 438-443

Bergveld, P., *Sens. Actuators, B* 2003, 88, 1-20

Bieri, C., Ernst, O. P., Heyse, S., Hofmann, K. P., Vogel H., *Nat Biotech,* 1999, 17, 1105-1108

Boukobza, E., Sonnenfeld, A., Haran, G., *J. Phys. Chem. B,* 2001, 105, 12165-12170

Cahen, D., Naaman, R., Vager, Z., *Adv. Functi. Mater.,* 2005, 15, 1571-1578

Capua, E., Natan, A., Kronik, L., Naaman, R., *ACS Appl. Mater. Interfaces,* 2009a, 1, 2679-2683

Capua, E., Cao, R., Sukenik, C. N., Naaman, R, *Sensor. Actual. B-Chem.,* 2009b, 140, 122-127

Chai, L., Cahen D., *Mat. Sci. Eng. C,* 2002, 19, 339-343

Chattopadhyay, A., Raghuraman, H., *Curr. Sci.,* 2004, 87, 175-180

Coldrick, Z., Penezic, A., Gasparovic, B., Steenson, P., Merrifield, J., Nelson, A., *J. Appl. Electrochem.,* 2011, 41, 939-949

Coughlin, J. F., Pope, J. E., Leedle, B. R., *Home Health Care Management & Practice,* 2006, 18(3), 196-207.

Dumas, C., Zein, R E., Dallaporta, H., Charrier, M., *Langmuir,* 2011, 27, 13643-13647

Fogt, E. J., Untereker, D. F., Norenberg, M. S., *Anal. Chem.,* 1985, 57, 1995-1998

Gartsman, K., Cahen, D., Kadyshevitch, A., Libman, J., Moav, T., Naaman, R., Shanzer, A., Umansky, V., Vilan, A., *Chem. Phys. Lett.,* 1998, 283, 301-306

Ghafar-Zadeh, E., Sawan, M., Chodavarapu, P. V., Hosseini-Nia, T., *IEEE Trans. Biomed. Circuits Syst.,* 2010, 4, 232-238

Goykhman, I., Korbakov, N., Bartic, C., Borghs, G., Spira, M. E., Shappir, J., Yitzchaik, S., *J. Am. Chem. Soc.,* 2009, 131, 4788-4794

Horcas, I., Fernandez, R, Gomez-Rodriguez, J. M., Colchero, J., Gomez-Herrero, J., Baro, A. M., *Rev. Sci. Instrum.,* 2007, 78, 013705

Ian, M., Gralnek, Barkun, A. N., Bardou, M., *N Engl J Med,* 2008, 359, 928-937

Janata, J., *Electroanalysis,* 2004, 16, 1831-1835

Kharitonov, A. B., Zayats, M., Lichtenstein, A., Katz, E., Willner, I., *Sens. Actuators, B* 2000, 70, 222-231

Kirchner, C., George, M., Stein, B., Parak, W. J., Gaub, H. E., Seitz, M., *Adv. Funct. Mater.,* 2002, 12, 266-276

Landefeld, C. S., Beyth, R. J., *The American Journal of Medicine,* 1993, 95, 315-328

Lazcka, O., Campo, F. J. D., Mufioz, F. X., *Biosensors and Bioelectronics,* 2007, 22, 1205-1217

Lee, C. S., Kim, S. K., Kim, M., *Sensors,* 2009, 9, 7111-7131

Makowski, M. S., Ivanisevic, A., *Small*, 2011, 7, 1863-1875
Mayer, T. K., Freedman, Z. R., *Clinica Chimica Acta*, 1983, 127, 147-184
McKinley, B. A., Houtchens, B. A., Janata, J., *Ion-Sel. Electrode Rev.*, 1984, 6, 173-208
McMurdy, J. W., Jay, G. D., Suner, S., Crawford, G. m *Clinical Chemistry*, 2008, 54, 264-272
Messing, E., *Urologic Oncology: Seminars and Original Investigations*, 2007, 25, 344-347
Naaman, R., *Phys. Chem. Chem. Phys.*, 2011, 13, 13153-13161
Park, H. D., Lee, K. J., Yoon, H. R., Nam, H. H., *Computers in Biology and Medicine*, 2005, 35, 275-286
Pflfflin, A., Schleicher, E., *Analytical and Bioanalytical Chemistry*, 2008, 393, 1473-1480
Price, C. P., *BMJ*, 2001, 322, 1285-1288
Rei Vilar, M., El-Beghdadi, J., Debontriddera, F., Naaman, R., Arbelc, A., Ferrariad, A. M., Botelho Do Rego, A. M., *Mat. Sci. Eng. C*, 2006, 26, 253-259
Richter, R. P., Berat, R., Brisson, A. R., *Langmuir*, 2006, 22, 3497-3505
Rother, R. P., *JAMA: The Journal of the American Medical Association*, 2005, 293, 1653-1662
Rudich, Y., Benjamin, I., Naaman, R., Thomas, E., Trakhtenberg, S., Ussyshkin, R., *J. Phys. Chem. A*, 2000, 104, 5238-5245
Sackmann, E., *Science*, 1996, 271, 43-48
Sackmann, E., Tanaka, M., *Trends Biotechnol*, 2000, 18, 58-64
Salimi, A., Hallaj, R., Khayatian, G., *Electroanalysis*, 2005, 17, 873-879
Sapuri, A. R., Baksh, M. M., Groves J. T., *Langmuir*, 2002, 19, 1606-1610
Schoning, M. J., Poghossian, A., *Analyst*, 2002, 127, 1137-1151
Tanaka, M., Sackmann, E., *Nature*, 2005, 437, 656-663
Thevenot, D. R., Toth, K., Durst, R. A., Wilson, G. S., *Biosens. Bioelectron.*, 2001, 16, 121-131
Thompson, M., Krull, U. J., *Anal. Chim. Acta*, 1982, 141, 33-47
Thompson, M., Krull, U. J., Bendell-Young, L. I., *Talanta*, 1983, 30, 919-924
Umezawa, Y., Kataoka, M., Takami, W., *Anal. Chem.*, 1988, 60, 2392-2396
Vilan, A., Ussyshkin, R., Gartsman, K., Cahen, D., Naaman, R., Shanzer, A. J., *Physic. Chem. B*, 1998, 102, 3307-3309
Vilan, A., Cahen, D., *Trends biotechnol.*, 2002, 20, 22-29
Wong, J. Y., Majewski, J., Seitz, M., Park, C. K., Israelachvili, J. N., Smith, G. S., *Biophys. J.*, 1999, 77, 1445-1457
Woodhouse, G., King, L., Wieczorek, L., Osman, P., Cornell, B., *J. Mol. Recognit.*, 1999, 12, 328-334
Wu, D. G., Ashkenasy, G., Shvarts, D., Ussyshkin, R. V., Naaman, R., Shanzer, A., Cahen, D., *Angew. Chem. Int. Ed.*, 2000, 39, 4496-4500
Wu, D. G., Cahen, D., Graf, P., Naaman, R., Nitzan, A., Shvarts, D., *Chem. Eur. J.*, 2001, 7, 1743-1749
Xu, Y., Bakker, E., *Langmuir*, 2009, 25, 568-573
Yip, C. M., Darabie, A. A., McLaurin, J., *J. Mol. Biol.*, 2002, 318, 97-107

The invention claimed is:

1. A semiconductor device for the detection of an active site-containing protein or a ligand thereof in a solution, said device being composed of at least one insulating or semi-insulating layer, at least one conducting semiconductor layer, two conducting pads, a protective molecular layer, and said ligand or active site-containing protein, wherein said at least one conducting semiconductor layer is on top of one of said insulating or semi-insulating layers, said two conducting pads are on both sides on top of an upper layer which is either one of said conducting semiconductor layers or another of said insulating or semi-insulating layers, making electrical contact with said at least one conducting semiconductor layer, said protective molecular layer is fabricated on top of said upper layer protecting said upper layer from corrosion, and said ligand or active site-containing protein is linked either directly or indirectly to said protective molecular layer, wherein exposure of said ligand or active site-containing protein, to a solution containing said active site-containing protein or ligand, respectively, causes a current change through the semiconductor device when a constant electric potential is applied between the two conducting pads.

2. A semiconductor device according to claim 1, composed of at least one insulating or semi-insulating layer, one conducting semiconductor layer, two conducting pads, a protective molecular layer, and said ligand or active site-containing protein, wherein said conducting semiconductor layer is on top of one of said insulating or semi-insulating layers, said two conducting pads are on both sides on top of an upper layer which is either said conducting semiconductor layer or another of said insulating or semi-insulating layers, making electrical contact with said conducting semiconductor layer, said protective molecular layer is fabricated on top of said upper layer, and said ligand or active site-containing protein is linked either directly or indirectly to said protective molecular layer.

3. A semiconductor device according to claim 1, for the detection of said active site-containing protein, wherein said device comprises said ligand linked either directly or indirectly to said protective molecular layer, and exposure of said ligand to a solution containing said active site-containing protein causes a current change through the semiconductor device when a constant electric potential is applied between the two conducting pads.

4. A semiconductor device according to claim 1, for the detection of said ligand, wherein said device comprises said active site-containing protein linked either directly or indirectly to said protective molecular layer, and exposure of said active site-containing protein to a solution containing said ligand causes a current change through the semiconductor device when a constant electric potential is applied between the two conducting pads.

5. A semiconductor device according to claim 1, wherein
(i) each one of said at least one conducting semiconductor layer independently is a semiconductor selected from the group consisting of a III-V and a II-VI material, or and a mixture thereof, wherein III, V, II and VI denote the Periodic Table elements III=Ga, In; V=As, P; II=Cd, Zn; VI=S, Se, Te; or
(ii) each one of said at least one insulating or semi-insulating layers independently is a dielectric material selected from the group consisting of silicon oxide, silicon nitride and an undoped semiconductor selected from the group consisting of a III-V and a II-VI material and a mixture thereof, wherein III, V, II and VI denote the Periodic Table elements III=Ga, In; V=As, P; II=Cd, Zn; VI=S, Se, Te.

6. A semiconductor device according to claim 5, wherein each one of said at least one conducting semiconductor layer is doped GaAs or doped (Al,Ga)As; or said undoped semiconductor is undoped GaAs or undoped (Al,Ga)As.

7. A semiconductor device according to claim 1, wherein said protective molecular layer comprises an alkoxysilane-based polymer formed by polymerization of dialkoxysilanes, trialkoxysilanes or tetraalkoxysilanes, each having a functional group, a biotinylated form thereof, or a mixture of the aforesaid.

8. A semiconductor device according to claim 7, wherein said polymer is formed by polymerization of dialkoxysilanes or trialkoxysilanes of the general formula $(C_1-C_7 \text{ alkyl})_2$-Si$(OR)_2$ or $(C_1-C_7 \text{ alkyl})$-Si$(OR)_3$, respectively, biotinylated forms thereof, or mixtures of the aforesaid, wherein each of the Rs independently is a $(C_1-C_4)$alkyl, preferably methyl or ethyl, and the $(C_1-C_7)$alkyl group of the trialkoxysilane, or one or two of the $(C_1-C_7)$alkyl groups of the dialkoxysilane, is substituted at a terminal carbon atom with a functional group selected from the group consisting of mercapto, amino, and hydroxyl; and is optionally further interrupted with one or more —NH— groups.

9. A semiconductor device according to claim 8, wherein said polymer is formed by polymerization of (i) a mercapto-functional alkoxysilane of the general formula HS—$(C_1-C_7)$alkylene-SiR$(OR)_2$ or HS—$(C_1-C_7)$alkylene-Si$(OR)_3$, preferably HS—$(C_1-C_7)$alkylene-Si$(OR)_3$, a biotinylated form thereof, or a mixture of the aforesaid, wherein each of the Rs independently is a $(C_1-C_4)$alkyl, preferably methyl or ethyl; (ii) an amino-functional alkoxysilane of the general formula $H_2N$—$(C_1-C_7)$alkylene-SiR$(OR)_2$ or $H_2N$—$(C_1-C_7)$alkylene-Si$(OR)_3$, preferably $H_2N$—$(C_1-C_7)$alkylene-Si$(OR)_3$, a biotinylated from thereof, or a mixture of the aforesaid, wherein each of the Rs independently is a $(C_1-C_4)$alkyl, preferably methyl or ethyl, and the $C_1-C_7$ alkylene is optionally interrupted with one or more —NH— groups; or (iii) a mixture of said mercapto-functional alkoxysilane and said amino-functional alkoxysilane.

10. A semiconductor device according to claim 9, wherein said mercapto-functional alkoxysilane is mercaptomethylmethyldiethoxysilane, mercaptomethyl methyldimethoxysilane, 3-mercaptopropylmethyldiethoxysilane, 3-mercaptopropyl methyldimethoxysilane, 3-mercaptopropyltrimethoxysilane (MPS), or 3-mercapto propyltriethoxysilane; and said amino-functional alkoxysilane is $N^1$-(3-(trimethoxysilyl)propyl)ethane-1,2-diamine, $N^1$-(3-(triethoxysilyl)propyl)ethane-1,2-diamine, 3-aminopropyltrimethoxysilane (APS), 3-aminopropyltriethoxysilane, 4-aminobutyltriethoxysilane, 4-aminobutyltrimethoxysilane, $N^1$-(3-(dimethoxy(methyl)silyl)-2-methylpropyl)ethane-1,2-diamine, $N^1$-(3-(diethoxy(methyl)silyl)-2-methylpropyl)ethane-1,2-diamine, aminopropylmethyldimethoxysilane, or aminopropylmethyldiethoxysilane.

11. A semiconductor device according to claim 10, wherein said polymer is formed by polymerization of a mixture of MPS and APS.

12. A semiconductor device according to claim 1, wherein said ligand or active site-containing protein is indirectly linked to said protective molecular layer via (i) a mono- or bi-layer membrane comprising an amphiphilic compound or a mixture thereof, wherein said mono- or bi-layer membrane is adhered to said protective molecular layer; or (ii) a linker selected from the group consisting of a ligand-binding protein such as Protein A, Protein G, streptavidin, avidin or an antibody, biotin, and a biotin-like molecule.

13. A device according to claim 12, wherein said ligand or active site-containing protein is (i) adsorbed to or incorporated into said mono- or bi-layer membrane; or (ii) linked to said protective molecular layer via a ligand-binding protein.

14. A semiconductor device according to claim 12, wherein said amphiphilic compound is a phospholipid selected from the group consisting of a phosphoglyceride or phosphosphingolipid, a biotinylated form thereof, and a mixture of the aforesaid.

15. A semiconductor device according to claim 14, wherein said phosphoglyceride is selected from the group consisting of a plasmalogen, a phosphatidate, a phosphatidylethanolamine, a phosphatidylcholine such as egg phosphatidylcholin (EPC), a phosphatidylserine, a phosphatidylinositol, phosphatidylinositol phosphate, phosphatidylinositol bisphosphate, phosphatidylinositol triphosphate, a glycolipid such as a glyceroglycolipid, glycosphingolipid, and glycosylphosphatidylinopsitol, a phosphatidyl sugar, and a biotinylated form thereof such as dioleoyl-sn-glycero-3-phosphoethanolamine-N-(cap biotinyl) (BCPE), Biotin-Phosphatidylcholine, Biotin Phosphatidylinositol 3-phosphate, Biotin Phosphatidylinositol 4,5-bisphosphate, Biotinylated phosphatidylinositol 3,4,5-trisphosphate, and 1-((1-octanoyl-N'-biotinoyl-1,6-diaminohexane-2R-octanoyl)phosphatidyl)inositol-3,4,5-triphosphate, tetrasodium salt; and said phosphosphingolipid is selected from the group consisting of a ceramide phosphorylcholine, a ceramide phosphorylethanolamine, a ceramide phosphorylglycerol, and a biotinylated form thereof such as Biotin Sphingomyelin.

16. A semiconductor device according to claim 1, wherein said solution is an aqueous solution, a physiological solution, a bodily fluid such as amniotic fluid, aqueous humour, vitreous humour, bile, blood serum, breast milk, cerebrospinal fluid, cerumen (earwax), endolymph, perilymph, female ejaculate, gastric juice, mucus, peritoneal fluid, saliva, sebum (skin oil), semen, sweat, tears, vaginal secretion, vomit and urine, or a bodily fluid-based solution.

17. A method for detection of an active site-containing protein or a ligand thereof in a solution, said method comprising:
  (i) exposing a semiconductor device according to claim 1 to said solution; and
  (ii) monitoring the presence of said active site-containing protein or ligand in said solution according to the changes in the current measured in said semiconductor device when a constant electric potential is applied between the two conducting pads.

18. The method of claim 17, for quantification of said active site-containing protein or ligand thereof in said solution, wherein the current change is proportional to the concentration of said active site-containing protein or ligand thereof in said solution.

19. The method of claim 17, for studying receptor-ligand pair interactions, in particular, monitoring the interaction of a receptor in a solution with a ligand linked either directly or indirectly to said protective molecular layer, or vice versa.

20. The method of claim 17, wherein (i) said active site-containing protein is an antibody, and said ligand is an antigen, or vice versa; (ii) said active site-containing protein is an enzyme, and said ligand is a substrate or inhibitor, or vice versa; (iii) said active site-containing protein is a receptor, and said ligand is a protein or organic molecule, or vice versa; or (iv) said active site-containing protein is a lectin, and said ligand is a sugar.

* * * * *